(12) United States Patent
Coleman et al.

(10) Patent No.: US 9,247,930 B2
(45) Date of Patent: Feb. 2, 2016

(54) DEVICES AND METHODS FOR OCCLUDING OR PROMOTING FLUID FLOW

(76) Inventors: James E. Coleman, Terenure (IE);
Christy Cummins, Naas (IE)

( * ) Notice: Subject to any disclaimer, the term of this patent is extended or adjusted under 35 U.S.C. 154(b) by 352 days.

(21) Appl. No.: 13/333,242

(22) Filed: Dec. 21, 2011

(65) Prior Publication Data
US 2013/0165963 A1    Jun. 27, 2013

(51) Int. Cl.
*A61B 17/03* (2006.01)
*A61B 17/00* (2006.01)
(Continued)

(52) U.S. Cl.
CPC ......... *A61B 17/0057* (2013.01); *A61B 17/0401* (2013.01); *A61B 17/11* (2013.01); *A61B 18/1492* (2013.01); *A61B 17/0487* (2013.01); *A61B 2017/00243* (2013.01); *A61B 2017/00575* (2013.01); *A61B 2017/00579* (2013.01); *A61B 2017/00592* (2013.01); *A61B 2017/00606* (2013.01); *A61B 2017/00619* (2013.01); *A61B 2017/00623* (2013.01); *A61B 2017/00986* (2013.01); *A61B 2017/042* (2013.01); *A61B 2017/0409* (2013.01); *A61B 2017/0412* (2013.01); *A61B 2017/0414* (2013.01); *A61B 2017/0422* (2013.01); *A61B 2017/0424* (2013.01); *A61B 2017/0464* (2013.01); *A61B 2017/0496* (2013.01);
(Continued)

(58) Field of Classification Search
CPC .......... A61B 17/0057; A61B 17/1214; A61B 17/12145; A61B 17/12168; A61B 2017/00986; A61B 2017/00575; A61B 2017/00623; A61B 2017/00592; A61B 2017/00606; A61B 2017/00619; A61B 2017/3484; A61B 17/08; A61B 17/12022

USPC ......... 606/151, 153, 155, 157, 158, 191, 194, 606/198, 213
See application file for complete search history.

(56) References Cited

U.S. PATENT DOCUMENTS

| 3,942,407 A | 3/1976 | Mortensen |
| 4,766,898 A | 8/1988 | Hardy et al. |

(Continued)

FOREIGN PATENT DOCUMENTS

| EP | 1908419 A1 | 4/2008 |
| WO | 0009040 A1 | 2/2000 |

(Continued)

OTHER PUBLICATIONS

Examination Communication from European Patent Office for Application No. 07 703 241.5 dated Apr. 30, 2009, 4 pgs.

(Continued)

*Primary Examiner* — Sarah W Aleman
(74) *Attorney, Agent, or Firm* — Mintz Levin Cohn Ferris Glovsky and Popeo, P.C.

(57) ABSTRACT

Devices and methods for occluding or promoting fluid flow through openings are disclosed. In one exemplary embodiment an occlusion device is provided having an expandable outer elongate tubular body, a guide member extending from a distal end of the outer body, and a slide tube disposed within the outer body, the proximal portions of the outer body and the slide tube being fixedly mated. The slide tube is configured to slide distally within the outer tubular body when the tubular body is expanded to form wings. A tether can be included as part of the device and it can be used to assist in positioning and locking a location of the device in an opening. Exemplary methods for delivering devices disclosed herein are also provided.

18 Claims, 15 Drawing Sheets

(51) Int. Cl.
*A61B 17/11* (2006.01)
*A61B 18/14* (2006.01)
A61B 17/42 (2006.01)
A61B 17/04 (2006.01)
A61B 17/22 (2006.01)
A61B 18/00 (2006.01)

(52) U.S. Cl.
CPC *A61B 2017/1107* (2013.01); *A61B 2017/1135* (2013.01); *A61B 2017/22044* (2013.01); *A61B 2017/22047* (2013.01); *A61B 2017/4233* (2013.01); *A61B 2018/00279* (2013.01); *A61B 2018/00351* (2013.01); *A61B 2018/00357* (2013.01)

(56) References Cited

U.S. PATENT DOCUMENTS

| | | | |
|---|---|---|---|
| 5,035,702 | A | 7/1991 | Taheri |
| 5,197,971 | A | 3/1993 | Bonutti |
| 5,222,963 | A | 6/1993 | Brinkerhoff et al. |
| 5,342,393 | A | 8/1994 | Stack |
| 5,496,332 | A | 3/1996 | Sierra et al. |
| 5,741,297 | A | 4/1998 | Simon |
| 5,853,422 | A | 12/1998 | Huebsch et al. |
| 6,024,756 | A | 2/2000 | Huebsch et al. |
| 6,117,159 | A | 9/2000 | Huebsch et al. |
| 6,183,496 | B1 | 2/2001 | Urbanski |
| 6,190,353 | B1 | 2/2001 | Makower et al. |
| 6,261,309 | B1 | 7/2001 | Urbanski |
| 6,312,446 | B1 * | 11/2001 | Huebsch et al. ............ 606/213 |
| 6,355,052 | B1 | 3/2002 | Neuss et al. |
| 6,375,671 | B1 | 4/2002 | Kobayashi et al. |
| 6,461,320 | B1 | 10/2002 | Yencho et al. |
| 6,616,685 | B2 | 9/2003 | Rousseau |
| 6,623,508 | B2 | 9/2003 | Shaw et al. |
| 6,632,237 | B2 | 10/2003 | Ben-David et al. |
| 6,666,873 | B1 | 12/2003 | Cassell |
| 6,776,785 | B1 | 8/2004 | Yencho et al. |
| 6,780,197 | B2 * | 8/2004 | Roe et al. ............ 606/213 |
| 6,942,674 | B2 | 9/2005 | Belef et al. |
| 6,960,224 | B2 | 11/2005 | Marino et al. |
| 6,994,713 | B2 | 2/2006 | Berg et al. |
| 7,018,388 | B2 | 3/2006 | Yencho et al. |
| 7,022,127 | B2 | 4/2006 | Suyker et al. |
| 7,108,702 | B2 | 9/2006 | Yencho et al. |
| 7,149,587 | B2 | 12/2006 | Wardle et al. |
| 7,608,086 | B2 | 10/2009 | Tanaka et al. |
| 7,625,392 | B2 * | 12/2009 | Coleman et al. ............ 606/213 |
| 7,798,992 | B2 * | 9/2010 | Ortiz ............ 606/108 |
| 7,803,195 | B2 | 9/2010 | Levy et al. |
| 7,833,280 | B2 | 11/2010 | Stack et al. |
| 7,846,174 | B2 | 12/2010 | Baker et al. |
| 7,892,214 | B2 | 2/2011 | Kagan et al. |
| 8,157,833 | B2 | 4/2012 | Au et al. |
| 8,192,457 | B2 | 6/2012 | Coleman et al. |
| 8,197,498 | B2 | 6/2012 | Coleman et al. |
| 8,366,742 | B2 | 2/2013 | Coleman et al. |
| 2002/0026137 | A1 | 2/2002 | Yencho et al. |
| 2002/0183768 | A1 | 12/2002 | Deem et al. |
| 2003/0158578 | A1 | 8/2003 | Pantages et al. |
| 2003/0171774 | A1 | 9/2003 | Freudenthal et al. |
| 2004/0116992 | A1 | 6/2004 | Wardle et al. |
| 2004/0122456 | A1 | 6/2004 | Saadat et al. |
| 2004/0243155 | A1 | 12/2004 | Yencho et al. |
| 2005/0043759 | A1 | 2/2005 | Chanduszko |
| 2005/0055050 | A1 | 3/2005 | Alfaro |
| 2005/0070935 | A1 * | 3/2005 | Ortiz ............ 606/153 |
| 2005/0075665 | A1 | 4/2005 | Brenzel et al. |
| 2005/0149071 | A1 | 7/2005 | Abbott et al. |
| 2005/0251209 | A1 | 11/2005 | Saadat et al. |
| 2005/0267524 | A1 | 12/2005 | Chanduszko |
| 2005/0273124 | A1 | 12/2005 | Chanduszko |
| 2005/0273135 | A1 * | 12/2005 | Chanduszko et al. ........ 606/213 |
| 2005/0277966 | A1 * | 12/2005 | Ewers et al. .................. 606/153 |
| 2005/0288786 | A1 | 12/2005 | Chanduszko |
| 2006/0047308 | A1 | 3/2006 | Ortiz et al. |
| 2006/0190036 | A1 | 8/2006 | Wendel et al. |
| 2006/0196137 | A1 | 9/2006 | Brenzel et al. |
| 2006/0211999 | A1 | 9/2006 | Fangrow |
| 2006/0217748 | A1 | 9/2006 | Ortiz |
| 2006/0265004 | A1 | 11/2006 | Callaghan et al. |
| 2007/0021758 | A1 | 1/2007 | Ortiz |
| 2007/0066863 | A1 | 3/2007 | Rafiee et al. |
| 2007/0106319 | A1 | 5/2007 | Au et al. |
| 2007/0129755 | A1 | 6/2007 | Abbott et al. |
| 2007/0185529 | A1 | 8/2007 | Coleman et al. |
| 2007/0233162 | A1 | 10/2007 | Gannoe et al. |
| 2008/0071376 | A1 | 3/2008 | Kohm et al. |
| 2008/0147101 | A1 | 6/2008 | Ortiz et al. |
| 2009/0088795 | A1 | 4/2009 | Cahill |
| 2009/0105733 | A1 | 4/2009 | Coleman et al. |
| 2010/0004681 | A1 | 1/2010 | Coleman et al. |
| 2010/0114128 | A1 | 5/2010 | Coleman et al. |
| 2010/0114156 | A1 | 5/2010 | Mehl |
| 2010/0256673 | A1 | 10/2010 | Coleman et al. |
| 2012/0245625 | A1 | 9/2012 | Coleman et al. |
| 2012/0265224 | A1 | 10/2012 | Coleman et al. |
| 2013/0131719 | A1 | 5/2013 | Coleman et al. |

FOREIGN PATENT DOCUMENTS

| | | |
|---|---|---|
| WO | 0149185 | 7/2001 |
| WO | 0205718 A2 | 1/2002 |
| WO | 03034927 A1 | 5/2003 |
| WO | 2007/013070 A1 | 2/2007 |
| WO | 2007/073566 A1 | 6/2007 |
| WO | 2007/088069 A1 | 8/2007 |
| WO | 2008/040577 A1 | 4/2008 |
| WO | 2009/052919 A2 | 4/2009 |

OTHER PUBLICATIONS

Form PCT/ISA/206 for Application No. PCT/EP2008/008178 dated Mar. 10, 2009, 6 pgs.
International Search Report and Written Opinion Application No. PCTEP2008008178 dated Aug. 6, 2009.
International Preliminary Report on Patentability and Written Opinion of the ISA dated Apr. 27, 2010, 13 pgs.
International Search Report and Written Opinion mailed May 28, 2013 for Application No. PCT/EP12/076029 (16 Pages).

* cited by examiner

DEVICES AND METHODS FOR OCCLUDING OR PROMOTING FLUID FLOW

FIELD

The present invention relates to devices and methods for occluding an opening or promoting fluid flow through an opening or conduit.

BACKGROUND

Catheterization and interventional procedures, such as angioplasty or stenting, generally are performed by inserting a hollow needle through a patient's skin and intervening tissue into the vascular system. A guidewire may then be passed through the needle lumen into the patient's blood vessel accessed by the needle. The needle may be removed, and an introducer sheath may be advanced over the guidewire into the vessel, e.g., in conjunction with or subsequent to a dilator. A catheter or other device may then be advanced through a lumen of the introducer sheath and over the guidewire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath are removed, leaving a puncture site in the vessel wall. External pressure may be applied to the puncture site until clotting and wound sealing occur. This procedure, however, may be time consuming and expensive, requiring as much as an hour of a physician or assistant's time. It is also uncomfortable for the patient and requires that the patient remain immobilized in the operating room, catheter lab, or holding area. Additionally, a risk of a hematoma exists from bleeding before hemostasis occurs. Accordingly, it can be desirable to seal the puncture using other techniques.

It can also be desirable to seal openings within a subject's body in other contexts as well. For example, in some instances it can be desirable to seal a fallopian tube to provide a form of birth control or disease prevention. It can also be desirable to seal openings that form in a body related to a defect or disease. Still further, in some instances it may be desirable to promote a flow of fluid through an opening, such as attaching a graft to a blood vessel. However, each of these techniques can be complicated by the limited nature of the space in which the procedures are to be performed and the devices and methods that currently exist for practicing such techniques.

By way of non-limiting example, one repair that is ripe for improvement is the treatment of a leaking mitral valve. The mitral valve includes two leaflets (anterior and posterior) attached to a fibrous ring or annulus. Contraction of the left ventricle in a healthy heart results in the mitral valve leaflets overlapping during contraction and prevention of blood flowing back into the left atrium. As a result of various medical cardiac diseases, the mitral value annulus may be come distended, causing the leaflets to remain partially open during ventricular contraction and thus allowing regurgitation of blood into the left atrium. In response to a reduced ejection volume from the left ventricle, the left ventricle tries to compensate with a large stroke volume. Eventually this increased workload results in dilation and hypertrophy of the left ventricle, further enlarging and distorting the shape of the mitral valve. The end result of this cardiac insufficiency if left untreated may be left ventricle failure and death. Current methods that exist for treatment of such conditions are limited.

Various apparatuses have been suggested for percutaneously sealing openings such as vascular punctures by occluding the puncture site, as well as for sealing other openings in a subject's body. One apparatus that exists for vascular closure is a biodegradable plug that is delivered through an introducer sheath into a puncture site. When deployed, the plug seals the vessel and provides hemostasis. Such plugs, however, may be difficult to position properly with respect to the vessel. Moreover, it is generally undesirable to expose the plugged material, e.g., collagen, to the blood stream where it may float down stream and risk causing an embolism. Another technique involves percutaneously suturing an opening. Percutaneous suturing devices, however, require significant skills by the user and can be mechanically complex and expensive to manufacture.

Other closure devices include surgical fasteners. One known surgical fastener includes an annular base having legs that, in a relaxed state, extend in a direction substantially perpendicular to a plane defined by the base and slightly inwards toward one another. During use, the fastener is fit around the outside of a cannula, thereby deflecting the legs outward. The cannula is placed in an incision, and the fastener is slid along the cannula until the legs pierce into the blood vessel. When the cannula is withdrawn, the legs move towards one another and back to the relaxed state to close the incision. Staples can also be used to close a wound or incision. Staples, however, tend to have a large cross-sectional profile and therefore may not be easy to deliver through a percutaneous site to close an opening in a vessel wall.

Accordingly, improved methods and devices for closing openings, including vascular puncture wounds, naturally existing openings in a subject's body, openings that result from defects or diseases, and surgically created openings, are needed. Improved methods and devices for promoting the flow of fluid through openings are also desirable.

SUMMARY

The present invention generally provides devices and methods for occluding an opening or promoting the flow of fluid through an opening. In one exemplary embodiment an occlusion device is provided having an outer elongate tubular body, a guide member extending distally from a distal end of the outer tubular body, and a slide tube disposed within the outer tubular body and having a proximal end that is fixedly mated to a proximal end of the outer tubular body. Both a proximal portion and a distal portion of the outer elongate tubular body can have a plurality of slits formed therein. The slits are configured to allow the proximal and distal portions to expand to form proximal and distal wings. The outer elongate tubular body can be configured to move along an outer surface of the slide tube as the proximal and distal portions expand to form the wings. In one embodiment the slits in the proximal portion can extend in a first direction around a circumference of the outer tubular body, and the slits in the distal portion can extend in a second, opposite direction around a circumference of the outer tubular body. The proximal and distal portions can be configured to expand in response to a torsional force that is applied to the outer elongate tubular body. A compressive force can also be applied to more fully form proximal and/or distal wings.

Optionally, a tether can be included as part of the device. The tether can have a distal portion disposed within the outer tubular body and a proximal portion that extends proximally from the proximal end of the outer tubular body. A locking tool can be coupled to the tether for the purpose of inducing tension in the tether.

The slide tube can have a variety of configurations, and in one embodiment the slide tube can be configured to occlude fluid flow through the proximal wings when the proximal portion of the outer tubular body is expanded. Similarly, the guide member can be configured to occlude fluid flow through the distal wings when the distal portion of the outer tubular body is expanded. A distal end of the slide tube can abut a proximal end of the guide member after the proximal and distal portions of the outer tubular body are expanded to form proximal and distal wings.

In one embodiment the device also includes an inner elongate tubular body that extends at least partially through the outer elongate tubular body and through the slide tube. A distal end of the inner elongate tubular body can be fixedly mated to the proximal end of the guide member. Alternatively, the distal end of the inner elongate tubular body can be fixedly mated to a distal tip on a distal end of the outer elongate tubular body. The inner elongate tubular body can include a frangible portion that allows a proximal portion of the inner tubular body to be separated from both a distal portion of the inner tubular body and the outer tubular body.

The device can also include an insertion guide that is configured to be coupled to the proximal portion of the inner elongate tubular body. The insertion guide can selectively expand and compress the outer elongate tubular body and/or activate the frangible portion of the inner elongate tubular body. In another embodiment, an insertion guide can extend through the outer elongate tubular body, distal of the guide member.

A distal tip can be disposed on a distal end of the guide member. In one embodiment the distal tip can be closed to occlude fluid from flowing through the outer elongate tubular body. Alternatively, at least one of the guide tube, the ejector tube, and the slide tube can be configured to occlude fluid from flowing through the outer elongate tubular body.

In another exemplary embodiment of an occlusion device, the device includes a core pin, an elongate tubular body coupled to the core pin and that has proximal and distal expandable portions, and a slide tube at least partially disposed within the elongate tubular body and having a proximal end that is mated to a proximal end of the elongate tubular body. The elongate tubular body can have at least two positions. In a first position, the proximal and distal portions are not expanded, and in a second position, the proximal and distal portions are expanded to form proximal and distal wings. As the elongate body is moved from the first position to the second position, it slides proximally over the slide tube to cause the core pin to move toward a distal end of the slide tube. In one embodiment, when the elongate body is in the second position, the distal portion of the slide tube abuts the core pin. The proximal and distal expandable portions of the elongate tubular body can have a plurality of slits formed therein.

The device can also include a distal tip that extends distally from the core pin. In another embodiment the device can include a tool that is configured to extend distally beyond the core pin. The tool can be used to form an opening in tissue. The device can also include an ejector tube disposed within the elongate tubular body. In one embodiment a distal portion of the ejector tube is coupled to the core pin. The ejector tube can be frangible such that its proximal portion is frangibly coupled to its distal portion.

The device can further include an insertion instrument that is configured to be coupled to the proximal portion of the ejector tube. The insertion instrument can selectively expand and compress the outer elongate tubular body and/or activate the frangible portion of the ejector tube. In another embodiment, an insertion instrument can extend through the outer elongate tubular body, distal of the core pin.

Optionally, a tether can be included as part of the device. The tether can be coupled to ejector tube, at either the tube's proximal or distal portion. A locking tool can be coupled to the tether for the purpose of inducing tension in the tether.

In other aspects, the slide tube can be configured to prevent fluid flow through the proximal wings of the outer tubular body. Similarly, the core pin can be configured to prevent fluid flow through the distal wings of the outer tubular body.

In one exemplary embodiment of a method for occluding an opening, the method includes advancing an elongate tubular body into an opening to be occluded, applying a first force to the elongate tubular body to cause a proximal portion of the elongate tubular body to expand and form proximal wings, and applying a second force to the elongate tubular body to cause a distal portion of the elongate tubular body to expand and form distal wings. Application of the first force can cause a distal end of the elongate tubular body to move a first distance in a proximal direction, and application of the second force can cause the distal end of the elongate tubular body to move a second distance in the proximal direction. In one embodiment, after the elongate tubular body moves the second distance, a slide tube disposed within at least a portion of the elongate tubular body abuts a distal guide member on the distal end of the elongate tubular body.

Application of the first force can include applying a rotational force in a first direction. Further, application of the second force can include applying a rotational force in a second, opposite direction. The elongate tubular body can include an inner tube that extends at least partially therethrough. In such an embodiment, the tubular body can be frangibly detached into a proximal portion and a distal portion, and the proximal portion can be removed from the elongate tubular body.

Optionally, a tether can be coupled to the elongate tubular body, or a component disposed therein, such as a slide tube or an inner tube. The tether can be tensioned, which can assist, for example, in setting and maintaining a desired position of the tubular body. In one embodiment, prior to advancing the elongate tubular body through the opening, the opening can be formed. Components of the device that includes the elongate tubular member can assist in forming the opening.

The opening to be occluded can be located in a number of different locations. By way of non-limiting example, the opening can be located in a fallopian tube, a heart, a blood vessel, or a tongue.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. In the present disclosure, like-numbered components of the embodiments generally have similar features, and thus within a particular embodiment each feature of each like-numbered component is not necessarily fully elaborated upon in the description of the particular embodiment. Further, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape.

Devices and methods for occluding an opening are generally provided. The opening can be a naturally existing opening, such as a fallopian tube, an opening resulting from a defect or a disease, such as a defect associated with heart disease, or an opening resulting from a puncture, such as a wound in a blood vessel. In an exemplary embodiment an occlusion device is provided having an outer elongate tubular body that is configured to expand and form wings proximate to opposed ends of the opening. The device can include a component to occlude flow through the tubular body, and thus through the opening. The component to occlude flow through the opening can be disposed within the outer elongate tubular body, or it can extend outside of the tubular body to block fluid flow before it even reaches the tubular body. Examples of occluding components include deployed distal and proximal wings of the outer elongate tubular body, a slide tube disposed within the outer elongate tubular body, a portion of an ejector tube disposed within the outer elongate tubular body, and one of a guide member or a distal tip extending distally from a distal end of the outer elongate tubular body.

Figure 1A:
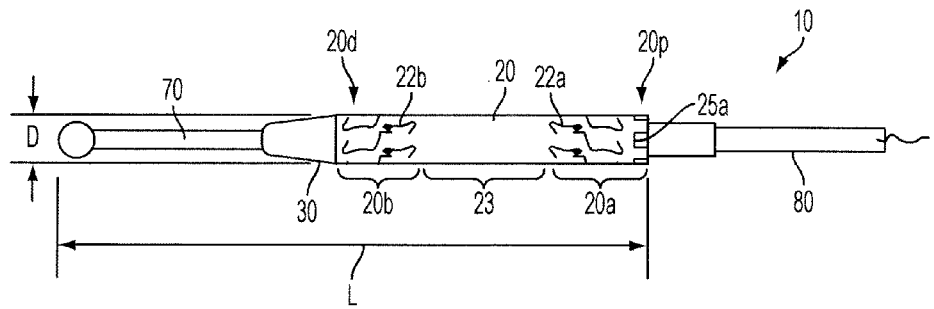
FIG. 1A is side view of one exemplary embodiment of an occlusion device in an initial, unformed configuration.
Figure 1B:
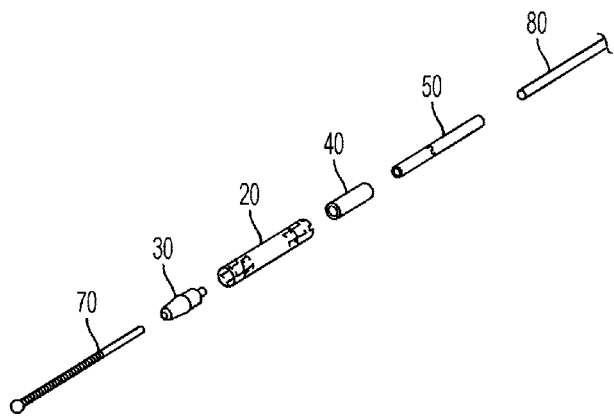
FIG. 1B is an exploded view of the device of FIG. 1A.

FIGS. 1A-10 illustrate one exemplary embodiment of an occlusion device 10 that can be used to occlude an opening. As shown in FIGS. 1A and 1B, the device 10 includes a generally elongate tubular body 20 having proximal and distal ends 20p, 20d and a number of components attached thereto and/or disposed therein. These components can include, for example, a guide member or core pin 30, a slide tube 40, an ejector tube 50, a distal tip or guide tip 70, and an insertion shaft or guide 80, each of which is discussed in greater detail below. Generally, the elongate tubular body 20 includes proximal and distal portions 20a, 20b that are configured to expand to engage tissue adjacent to an opening therebetween, while one or more of the components attached to and/or disposed in the tubular body 20 are configured to occlude the opening in which the device 10 is disposed. The portions 20a, 20b of the body 20 that are configured to expand, e.g., wings 24a, 24b, can also occlude the opening.

FIGS. 2-6 illustrate the outer elongate tubular body 20 in more detail. As illustrated in the undeployed configuration in FIG. 2, the proximal and distal portions 20a, 20b each include a plurality of slits 22a, 22b formed therein and configured to allow portions of the elongate tubular body 20 between the pluralities of slits 22a, 22b to radially expand. A mid-portion 23 of the tubular body 20, located between the proximal and distal portions 20a, 20b, can be slit-free and it can be configured to be positioned within an opening to be occluded. The mid-portion 23 can have a fixed or adjustable length that corresponds to a thickness of the tissue walls.

Figure 8:
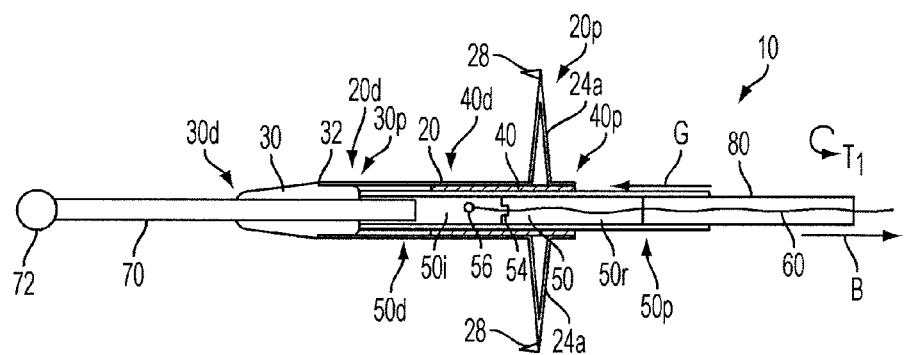
FIG. 8 is a side cross-sectional view of the device of FIG. 7 in a partially formed configuration.
Figure 9:
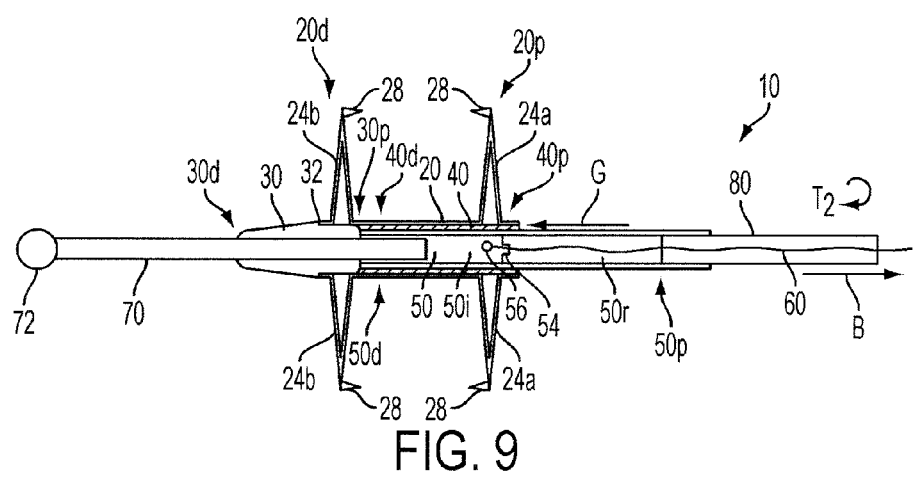
FIG. 9 is a side cross-sectional view of the device of FIG. 8 in a fully formed configuration with an insertion guide coupled thereto.
Figure 10:
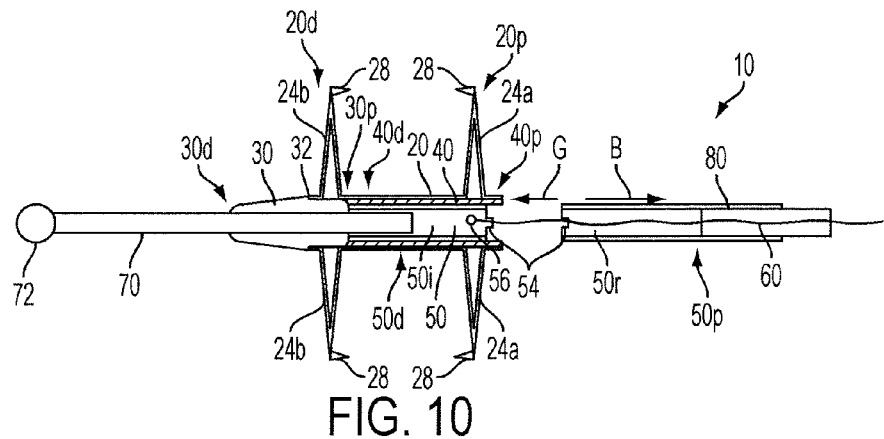
FIG. 10 is a side cross-sectional view of the device of FIG. 9 in a fully formed configuration with an insertion guide detached therefrom.

The slits 22a, 22b in the proximal and distal portions 20a, 20b can extend in any direction, and each portion 20a, 20b can include any number of slits. Preferably, the slits 22a, 22b are configured such that certain portions of the elongate tubular body 20 between the slits 22a, 22b will extend outward away from a central axis A of the tubular body 20 when the body 20 is axially compressed and/or rotated. As a result, one or more wings 24a, 24b will form in each of the distal and proximal portions 20a, 20b to engage tissue therebetween to assist in establishing and maintaining a location of the device 10. The device 10 can also include tabs 25a in the proximal portion 20a to aid in forming the wings, as discussed further below. Tabs can likewise be formed in distal portion 20b if desired. In some embodiments, as shown in FIGS. 8-10, the wings 24a, 24b can include tissue-engaging tangs 28 that extend generally perpendicular to the formed wing and provide further assistance in maintaining a location of the device 10.

Figure 2:
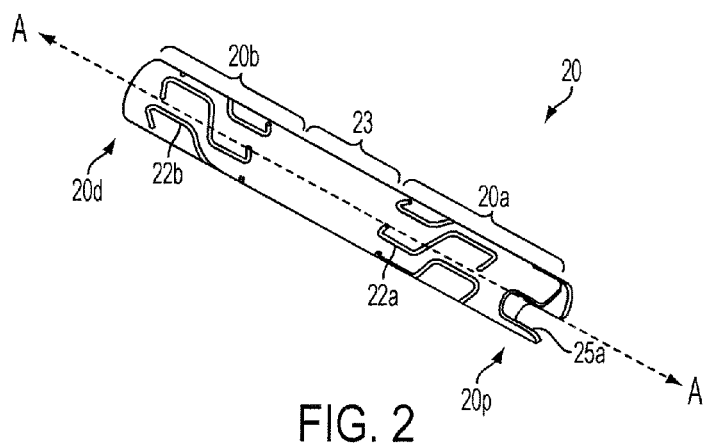
FIG. 2 is a perspective view of an outer elongate tubular member of the device of FIG. 1 in an initial, unformed configuration.

In an exemplary embodiment, as shown in FIG. 2, the slits 22a, 22b can be substantially S-shaped. The slits 22a, 22b can extend longitudinally along the elongate tubular body 20 in a proximal-distal direction, and they can be spaced axially around the elongate tubular body 20. More preferably, the slits 22a in the distal portion 20a can extend in a first direction around a circumference of the elongate tubular body 20 and the slits 22b in the proximal portion 20b can extend in a second, opposite direction around the circumference of the elongate tubular body 20. Such a configuration allows the tubular body 20 to be rotated in a first direction to cause only one of the proximal and distal portions 20a, 20b to radially expand, and then to be rotated in a second, opposite direction to cause the other one of the proximal and distal portions 20a, 20b to radially expand. The proximal and distal portions 20a, 20b can be adapted to move towards one another as they expand upon rotation and are compressed into shape, thereby allowing the wings to engage tissue therebetween.

Figure 3:
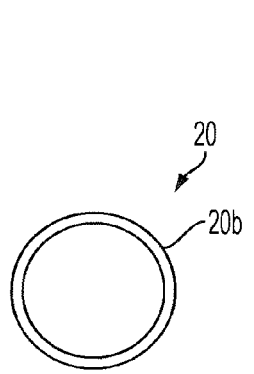
FIG. 3 is an end view of the tubular member of FIG. 2 prior to deployment.
Figure 4:
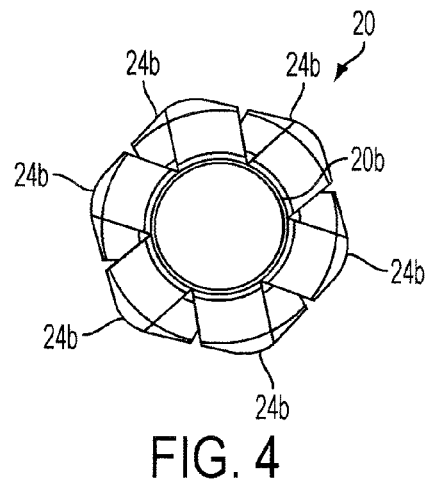
FIG. 4 is an end view of the tubular member of FIG. 2 following deployment.

FIGS. 3 and 4 show distal end views of the tubular body 20 in its pre-deployed configuration and following partial or full deployment, respectively. In the pre-deployed configuration shown in FIG. 3, the elongate tubular body 20 has a diameter that is configured to fit within an opening. FIG. 4 illustrates the distal portion 20b radially expanded to form the distal wings 24b. When the proximal portion 20a is radially expanded to form the proximal wings 24a, the proximal wings 24a can be aligned with the distal wings 24b to facilitate lumen joining. In such a case, the distal end view of the tubular body 20 would look as shown in FIG. 4 both before and after deployment of the proximal wings 24a. The proximal wings 24a can also be offset radially from the distal wings. In the illustrated embodiment, the slits 22a, 22b are configured such that the proximal and distal portions 20a, 20b each include six wings, however the proximal and distal portions can include any number of wings.

Figure 5:
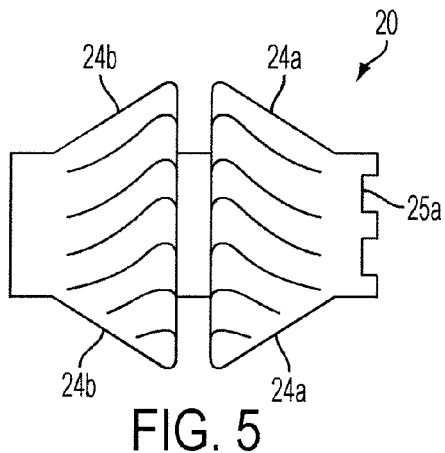
FIG. 5 is a side view of the tubular member of FIG. 2 following deployment.

FIG. 5 shows the outer tubular body 20 in a deployed configuration. In the deployed configuration, the proximal portion 20a is expanded to form proximal wings 24a, and the distal portion 20b is expanded to form distal wings 24b. The wings 24a, 24b are formed by the material between the slits 22a, 22b, which is deformed outward as the outer elongate body 20 is rotated and then compressed. The wings 24a, 24b can be concurrently or sequentially formed, e.g., deploying the distal wings 24b before the proximal wings 24a. Further, the middle portion 23 can optionally be compressed by applying an axial force to the outer tubular body 20, thereby decreasing the distance between the wings 24a, 24b. This can be achieved, for example, by forming the mid-portion 23 from telescoping tubes.

Figure 6:
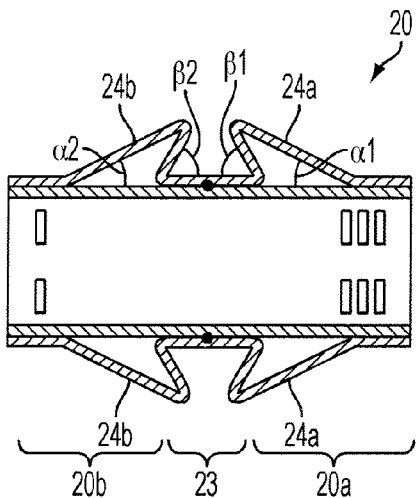
FIG. 6 is a side cross-sectional view of the tubular member of FIG. 2 following deployment.

FIG. 6 shows a cross-sectional view of the deployed tubular body 20 of FIG. 5. The asymmetric profile of the slits 22a, 22b can allow the wings 24a, 24b to form such that interior base bend angles $\alpha 1$, $\alpha 2$ are less than respective exterior base bend angles $\beta 1$, $\beta 2$. As a result, the wings 24a, 24b will also extend toward one another. The interior based bend angles $\alpha 1$, $\alpha 2$ can be the same or different in the proximal and distal portions 20a, 20b, as can the exterior base bend angles $\beta 1$, $\beta 2$. If the exterior base bend angles $\beta 1$, $\beta 2$ are each about 90 degrees, the wings 24a, 24b extend substantially parallel to each other, while acute and obtuse exterior base bend angles $\beta 1$, $\beta 2$ can allow the wings 24a, 24b to be angled toward each other at one end and away from each other at the opposite end. A person skilled in the art will recognize that the slits can have multiple configurations such that certain portions of the wings are perpendicular to the middle portion of the device with other portions of the wings are inclined toward or away from each other.

Alternative configurations for elongate tubular bodies that can be used in conjunction with the teachings herein can be found at least in U.S. Pat. No. 7,625,392 to Coleman et al., entitled "Wound Closure Devices and Methods," and U.S. Patent Application Publication No. 2010/0114128 of Coleman et al., entitled "Gastric Bypass Devices and Procedures," the contents of each which are each incorporated by reference in their entireties. A person skilled in the art would understand how to incorporate the teachings of these various embodiments into the devices and methods disclosed herein without departing from the spirit of the invention.

The distal end 20d of the tubular body 20 can be coupled to a guide member or core pin 30, which can be provided to assist in guiding the device 10 to its desired location and/or to assist in occluding an opening in which the device 10 is disposed. In the illustrated embodiment the core pin 30 is generally cylindrical, hollow, and includes a bore extending therethrough. A distal end 30d of the core pin 30 can be tapered in the distal direction as shown to assist in guiding the device 10 to a desired location. The core pin 30 can also include a stop surface 32, which can prevent the tubular body 20 from further distal travel when a compressive force is applied to it. As shown in FIGS. 7-10, the distal end 20d of the tubular body 20 can be coupled to the core pin 30 at the stop surface 32. Further, as illustrated, the core pin 30 can optionally extend into a portion of the elongate tubular body 20. While in the illustrated embodiment the core pin 30 is generally hollow and includes a bore extending therethrough, in other embodiments the core pin 30 can be solid or closed such that it is a component of the device 10 that occludes an opening in which the device 10 is disposed.

Figure 7:
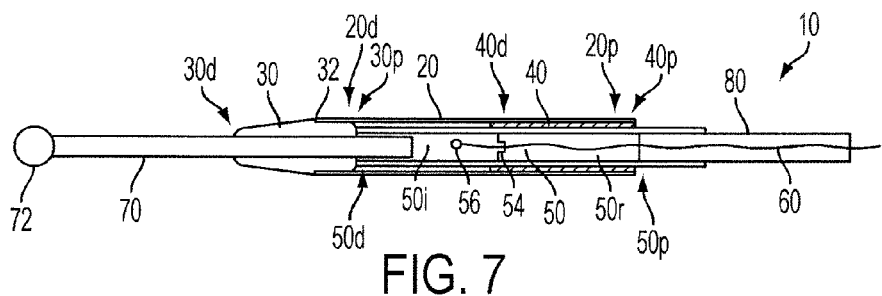
FIG. 7 is a side cross-sectional view of the occlusion device of FIG. 1 in the initial, unformed configuration.

As further shown in FIGS. 7-10, a slide tube 40 can be disposed within the outer elongate tubular body 20. The slide tube 40 can be configured to slide within the device 10 and assist in both the actuation and occlusion of the device 10. In the illustrated embodiment the slide tube 40 is generally cylindrical in shape and includes a bore therethrough so that the tube 40 can receive a shaft, such as the ejector tube 50, along which the tube 40 can slide. As shown in FIG. 7, the slide tube 40 can extend distally such that it extends beyond the proximal slits 22a when the tubular body 20 is not deployed. Further, when the proximal wings 24a are formed, for instance in FIGS. 8-10, the slide tube 40 can remain disposed across an opening below the formed wings 24a to occlude fluid from passing into the expanded wings 24. Likewise, as shown in FIGS. 9 and 10, the core pin 30 can occlude fluid from passing into the expanded distal wings 24b. As a result, fluid traveling through the internal bore of the implant cannot migrate through the slots in the base of the distal and proximal wings 24b, 24a as these are sealed by the core pin 30 and the slide tube 40.

In one embodiment, a proximal end 40p of the slide tube 40 is coupled to the proximal end 20p of the tubular body 20 such that forces applied to the slide tube 40 are translated to the tubular body 20. For example, if a torsional force in the direction $T_1$ is applied to the proximal end 40p of the slide tube 40, then the force can be translated to the proximal end 20p of the tubular body 20. Likewise, if an axial force in the direction G is applied to the proximal end 40p, then the force can be translated to the proximal end 20p. Alternatively, the torsional and compressive forces can be applied to the tubular body 20, which can then translate to the adjoining slide tube 40. As shown in FIGS. 7-10, as the axial force is applied to the device 10 in the direction G, the slide tube 40 slides distally toward the core pin 30, and the proximal end 20p of the tubular body 20 also moves distally while the body 20 expands to form the wings 24b, 24a.

In an alternative embodiment, the slide tube 40 can be configured to remain substantially stationary while the outer elongate tubular body 20 slides along an outer surface of the slide tube 40. The proximal end 40p of the slide tube can be coupled to the proximal end 20p of the tubular body 20. The core pin 30, which can be mated to the distal end 20p of the tubular body 20, can be configured to slide toward the slide tube 40 to actuate the wings 24 of the tubular body 20. While the actuation of the wings 24 is described in more detail below, in this alternative embodiment, sliding the core pin 30 toward the slide tube 40 can cause a first force to be applied to the outer elongate tubular body 20 such that the body 20 moves a first distance in a proximal direction to expand and form the proximal wings 24a, and sliding the core pin 30 further toward the slide tube 40 can cause a second force to be applied to the outer elongate tubular body 20 such that the body 20 moves a second distance in a proximal direction to expand and form the distal wings 24b. A person skilled in the art will recognize that the devices and procedures associated with actuation of the outer elongate tubular body 20 can be modified, for instance, actuating the distal wings 24b prior to the proximal wings 24a, without departing from the spirit of the invention based, at least in part, on the other components associated with the body 20, the direction of the forces being applied to the body 20, and the desired deployment order of the wings 24.

As further shown in FIGS. 7-10, the device 10 can include an ejector tube 50 disposed in the outer elongate tubular body 20 such that the slide tube 40 can slide along it. The ejector tube 50 can be substantially solid throughout to provide occlusion of the opening in which it is disposed. Generally, the ejector tube 50 can include two portions, an implant portion 50i and a removable portion 50r. In an exemplary embodiment the ejector tube 50 is frangible at a separable break 54, which divides the distal implant portion 50i from the proximal removable portion 50r. The separable break 54 can be a weakened portion of the ejector tube 50, thereby allowing the ejector tube 50 to be frangible. Following deployment of the device 10 in an opening, the ejector tube 50 can be broken into the two portions 50i and 50r and the removable portion 50r can be removed from the implant.

In the embodiment illustrated in FIGS. 1B and 7-10, a proximal end 50p includes a bore for receiving an insertion instrument, and a distal end 50d includes a bore for receiving a guide tip 70 and a proximal end 30p of the core pin 30. Optionally, a tether attachment 56, such as a bore, can be provided on the ejector tube 50 to allow a tether 60 to be coupled to the device 10. In the illustrated embodiment the tether attachment 60 is located on the implant portion 50i so the tether 60 can remain with the implant even after the removable portion 50r is removed. In other embodiments a tether attachment can be included as part of the removable portion 50r so a tether associated therewith can be removed after implantation. Further, a tether attachment can be included with any of the other removable or implanted components of the device 10 as desired.

As shown in FIGS. 7-10, the distal end 50d of the ejector tube 50 can be coupled to a proximal end 30p of the core pin, and the proximal end 50p can receive an insertion instrument. Although in the illustrated embodiment the proximal end 50p extends beyond the proximal end 20p of the tubular body 20 when the tubular body is in an undeployed configuration, in other embodiments the proximal end 50p may be flush with or terminate prior to the proximal end 20p. As a result of this configuration, forces applied to the insertion instrument can be applied to the ejector tube 50, which in turn can be translated to each of the core pin 30, the slide tube 40, and the tubular body 20.

The tether 60 can optionally be associated with the occlusion device 10, for instance by attaching to the device 10 at the tether attachment 56. The tether 60 can extend proximally from the occlusion device 10 and can assist in locating the device 10 at a desired location by acting as a tensioning member. For example, a user can pull the tether to position the device 10 at a desired location, or the tether 60 can work in conjunction with a locking tool or mechanism 90 to assist in maintaining a location of the device 10, as described in greater detail below. The tether 60 can be selectively disassociated from the device 10 as desired. Further, in embodiments in which the tether is not configured to remain as part of the implant, the tether 60 can be configured to pull from the surgical site one or more of the components of the device or system intended to be removed, such as the removable portion 50r of the ejector tube 50. Even when the tether 60 is configured to remain as part of the implanted portion of the device 10, the tether 60 can be used to remove the device 10 from the opening in which it is implanted at a later time.

A further component that can be used to help navigate the occlusion device 10 to a desired location is an optional guide tip 70. As shown, the guide tip 70 is coupled to the proximal end 30p of the core pin 30, which in turn is coupled to the distal end 50d of the ejector tube 50. The guide tip 70 can extend through and distally beyond a distal end 30d of the core pin 30. The guide tip 70 can be substantially solid, thereby occluding the opening in which the device 10 is disposed. A terminal end 72 of the guide tip 70 can have a variety of shapes to assist in providing occlusion, but in the illustrated embodiment the terminal end 72 is substantially spherical and has a diameter configured to occlude an opening. In an exemplary embodiment, the diameter of the terminal end 72 is larger than a diameter of the elongate body of the guide tip 70. The guide tip 70 can also be substantially flexible to assist in navigation of the occlusion device 10 through a tortuous lumen.

Yet another component that can be used to help navigate the occlusion device 10 to a desired location is an optional proximal insertion guide 80. As shown, the insertion guide 80 can be substantially elongate and solid, and, similar to the guide tip 70, can be substantially flexible to assist in navigation of the occlusion device 10. The insertion guide 80 can be formed from various rigid and/or flexible materials, such as Nitinol® or stainless steel. In use, the insertion guide 80 can be removably and replaceably coupled to the proximal end 50p of the ejector 50 and extend proximally therefrom toward an insertion instrument. The insertion guide 80 can act as a tensioning member capable of allowing axial and rotational force to be transmitted therethrough and thus to the elongate tubular body 20.

Figure 11A:
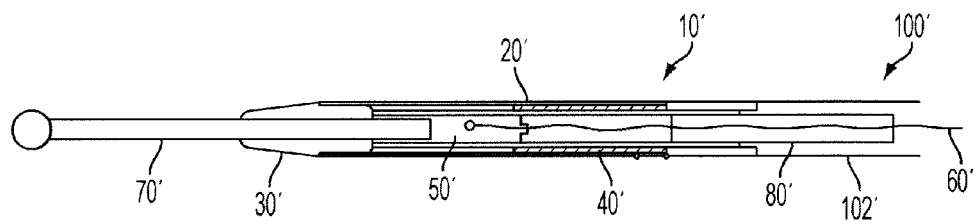
FIG. 11A is a side cross-sectional view of another exemplary embodiment of an occlusion device in an initial, unformed configuration with a former coupled thereto.
Figure 11B:
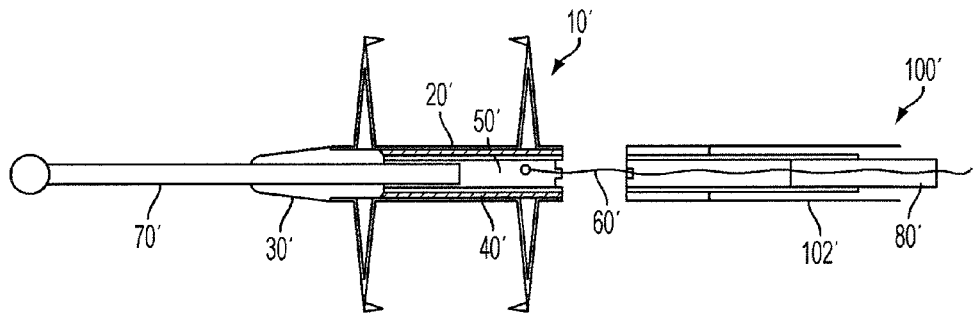
FIG. 11B is a side cross-sectional view of the device of FIG. 11A in a fully formed configuration with a former detached.

The proximally extending portion of the insertion guide 80 can be received by an instrument for inserting and/or deploying the occlusion device 10. In one embodiment illustrated in FIGS. 11A and 11B, the insertion instrument includes a former 100' having an outer shaft 102' and a bore extending therethrough in which the insertion guide 80' can be disposed to couple the former 100' to the occlusion device 10'. The device 10' can include many of the same components as the device 10, including an elongate tubular body 20', a core pin 30', a slide tube 40', an ejector tube 50', a tether 60', and a guide tip 70'. A further connection between the former 100' and the occlusion device 10' can also be made between the former 100' and the elongate tubular body 20'. A distal end 102d' of the outer shaft 102' can include receiving protrusions configured to be complementary to tabs (similar to the tabs 25a of the device 10) at the proximal end of the elongate tubular body 20' so that the former 100' can be selectively coupled and de-coupled to the occlusion device 10'.

In one embodiment, the insertion guide 80' can be rotatably disposed within the outer shaft 102' to allow the insertion guide 80° to selectively apply compressive forces and/or torsional forces to the elongate tubular body 20'. Following implantation, the outer shaft 102' can be disconnected from the occlusion device 10', for instance by disengaging the protrusions 103' from the tabs 25a' and by disconnecting the insertion guide 80' from the former 100'. In the illustrated embodiment the former 100' is disconnected from the occlusion device 10' after the ejector tube 50' is separated into two portions. The former 100', which is slidably coupled to the insertion guide 80', which itself is coupled to the removable portion 50r' of the ejector tube 50', is pulled proximally away from the occlusion device, thereby disassociating the removable portion 50r', the insertion guide 80', and the former 100' from the occlusion device 10'. In one alternative embodiment, the insertion guide can remain attached to the portion of the device that remains at the implant location, for instance to assist with later guiding and tensioning of the device in lieu of or in addition to a tether.

Figure 11C:
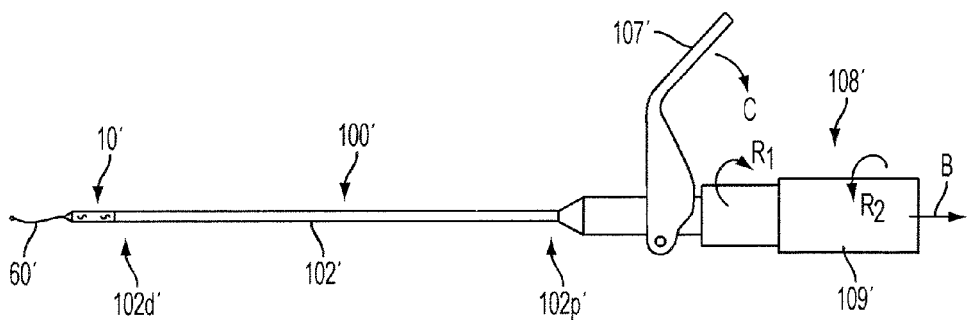
FIG. 11C is a side view of a delivery system coupled to the device and former of FIG. 11A.

The former 100' can be an insertion instrument on its own. Alternatively, the former 100' can be part of a delivery system configured to actuate the former and the insertion guide, and thereby the occlusion device. One exemplary embodiment of such a delivery system is illustrated in FIG. 11C. As shown, the former 100' is coupled to the occlusion device 10' at the distal end 102d' of former shaft 102', and is coupled to an actuator 108' at a proximal end 102p' of the former shaft 102'. The actuator 108' can be configured to apply various forces to the insertion guide 80' and the former 100', and thus the occlusion device 10'. For example, the actuator 108' can include a handle 109' coupled to the insertion guide 80' and configured to apply a first torsional force to the insertion guide 80' when the handle 109' is rotated in a first direction $R_1$ to cause the insertion guide 80' to rotate. The handle 109' can also be configured to apply a compressive force to the insertion guide 80' in a direction B after rotation of the handle 109' in the first direction $R_1$ is complete. This actuation can cause wings of an occlusion device to be formed. The handle 109' can also be rotated in a second, opposite direction $R_2$ to apply a second torsional force, which can be followed by application of a compressive in the direction B to deploy a second set of wings of an occlusion device. In other embodiments, separate controls can exist for applying the torsional and compressive forces. The delivery system can also include a lever 107' configured to separate an ejector tube into an implant portion and a removable portion. As shown, the lever 107' can be rotated in a direction C, to exert a force on the handle 109' in the direction B. This movement can cause a tensile force to be exerted on the insertion guide 80' and a compressive force on the former 100', thereby breaking an ejector tube at its separable break. The delivery system can include other controls as well, such as controls to selectively tension the tether 60'. A person skilled in the art will recognize a number of other designs and types of insertion instruments, formers, and delivery systems can be used to deploy in openings the devices of the nature described herein. By way of non-limiting example, the formers and insertion instruments disclosed in U.S. Pat. No. 7,625,392 and U.S. Patent Application Publication No. 2010/0114128 of Coleman et al., which were previously incorporated by reference in their entireties, can be configured for use with the devices disclosed herein.

Figure 12:
FIG. 12 is a side view of one exemplary embodiment of a locking mechanism for use with the occlusion device of FIG. 1.
Figure 13A:
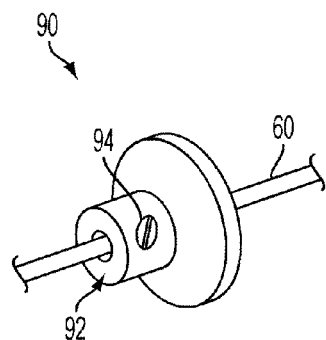
FIG. 13A is a perspective view of the locking mechanism of FIG. 12.

As shown in FIGS. 12 and 13A, a locking mechanism or tool can optionally be attached to the tether 60 to assist in maintaining a location of the device 10 within the body. The locking mechanism 90 can be configured to slide along the tether 60 in two directions and to selectively lock on the tether 60 to induce tension in the tether 60. Inducing tension in the tether 60 can induce tension on the occlusion device 10, thereby allowing the occlusion device 10 to be maintained at a desired location. The locking mechanism 90 can initially be connected to the tether 60, or it can be attached to the tether 60 at any time during a surgical procedure.

In the embodiment illustrated in FIGS. 12 and 13A, the locking mechanism 90 is cylindrical in shape and includes a threaded bore 92 for passage of the tether 60 and a threaded fastener 94 to selectively engage the tether 60 to lock and unlock the locking mechanism 90. As shown, the threaded fastener 94 can be rotated to tighten, which causes the tether 60 to clamp in position within the locking mechanism 90 to lock the tether 60. The threaded fastener 94 can be rotated in opposite direction to disengage the locking mechanism 90 and tether 60, thereby allowing the tether 90 to slide freely along the tether 60 in either direction. In an alternative embodiment, the threaded fastener 94 can be replaced by a button that is selectively biased to engage and thus tension the tether 60. Pushing the button inward toward the tether 60 allows the locking mechanism 90 to slide in either direction along the tether 60. The button can then be released to lock the locking mechanism 90 on the tether 60 and again tension the tether 60.

Figure 13B:
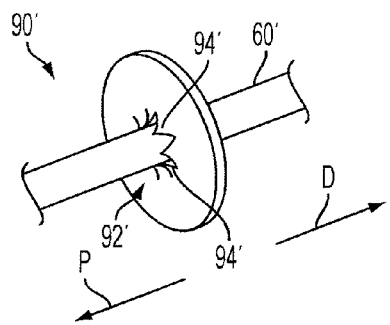
FIG. 13B is a perspective view of an alternative embodiment of a locking mechanism.

Another alternative embodiment of a locking mechanism is illustrated in FIG. 13B. As shown, the locking mechanism 90' is disc-shaped, has a bore 92' disposed therein for passage of the tether 60', and includes a plurality of tangs 94' extending in a proximal direction P. The configuration of the tangs 94' is such that the locking mechanism 90' can only travel in a distal direction D, thereby further tensioning the tether 60', because any force applied in the proximal direction will cause the tangs 94' to direct down onto the tether 60' and lock it into position.

Figure 13C:
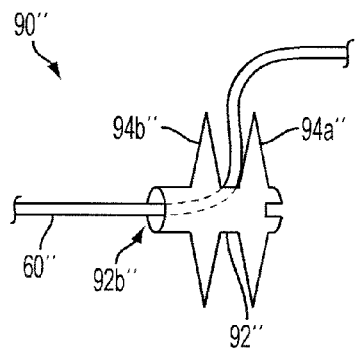
FIG. 13C is a side, partially transparent view of a further alternative embodiment of a locking mechanism.

FIG. 13C illustrates yet another embodiment of a locking mechanism 90". This locking mechanism 90" operates similar to the anchoring and occlusion device 10. It includes an elongate tubular body 92" having a bore 92b" disposed therein and is configured to deploy proximal and distal wings 94a" and 94b" in manners described herein with respect to similarly formed devices. As shown, the tether 60" can be disposed through at least a portion of the locking mechanism 90". In one exemplary embodiment, the distal wings 94b" can first be deployed and then pushed against tissue to create tension in the tether 60". Once the desired tension in the tether 60" is achieved, then the proximal wings 94a" can be deployed, thereby locking the tether 60" between the wings 94a" and 94b".

Figure 14:
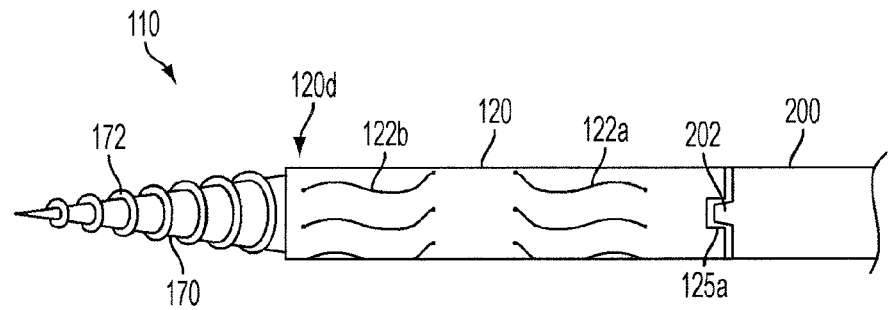
FIG. 14 is a side view of one exemplary embodiment of an occlusion device in the initial, unformed configuration.

Another embodiment of a device is illustrated in FIG. 14. The device 110 includes many of the same components as device 10, including the illustrated outer elongate tubular body 120 having a plurality of slits 122b, 122a formed therein and a former 200 having one or more protrusions 202 configured to engage notches 125a of the outer tubular body 120. In this embodiment, however, the distal tip 170 of the illustrated embodiment is a conical member having a helical thread 172 extending across a majority of the distal tip 170. The distal tip 170 can be attached to a distal end 120d of the outer tubular body 120, or alternatively, to one or more components disposed within the tubular body 120, such as an ejector tube (similar to the ejector tube 50) or an insertion guide (similar to the insertion guide 80). The distal tip 170 can be used to puncture tissue to create an opening in which to dispose the occlusion device 110. The distal tip 170 can be rotated in a clockwise direction to cause the helical threads 172 to advance the device 110 into the punctured tissue. Upon positioning the device 110 at the desired location, wings of the outer tubular body 120 can be deployed as described herein. In one embodiment, the distal tip 170 can be disposed in a hard material, such as bone, to prevent movement of the tubular body 120 when forces are applied to the device 110. In such an embodiment, the distal tip 170 can serve a purpose similar to the stop surface 32d and the proximal end 30p of the core pin 30, i.e., it can prevent distal movement of the outer elongate tubular body 120.

Figure 15A:
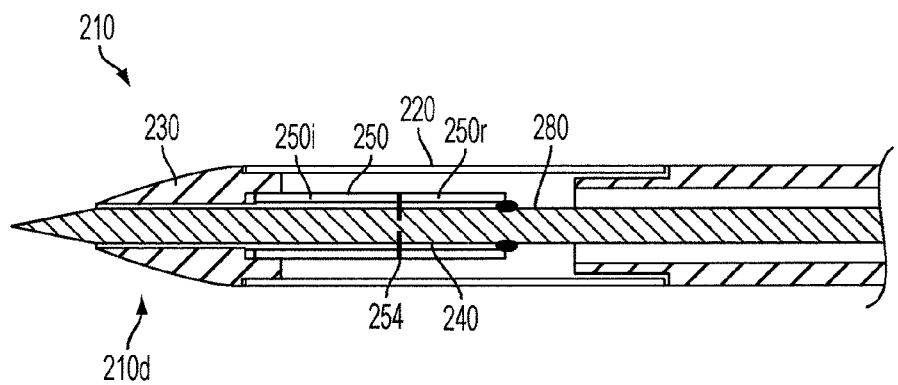
FIG. 15A is a side cross-sectional view of one exemplary embodiment of a deployment device in an initial, unformed configuration.
Figure 15B:
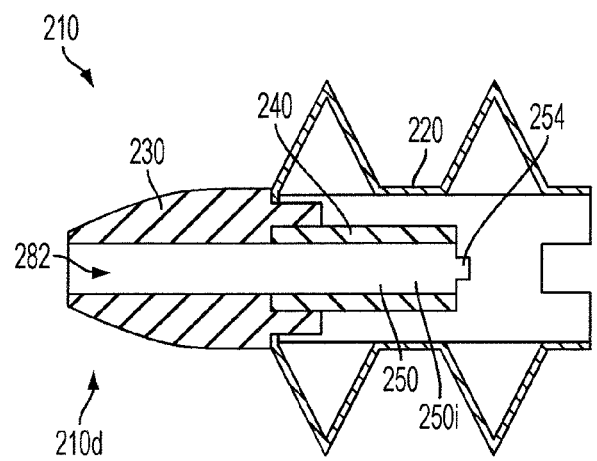
FIG. 15B is a side cross-sectional view of the device of FIG. 15A in a fully formed configuration.

In another embodiment of a deployment device, illustrated in FIGS. 15A and 15B, an insertion guide 280 can extend beyond a distal end 210d of the device 210. As shown in FIG. 15A, prior to deployment of the device 210, the insertion guide 280 extends through the entirety of the outer elongate tubular body 220, the slide tube 240, the ejector tube 250, and the core pin 230. Accordingly, in this embodiment, the ejector tube 250 includes a bore disposed therethrough, and its break point 254 is located therein. The insertion guide 280 is removably coupled to a removable portion 250r of the ejector tube 250. After wings of the outer tubular body 220 are formed, the ejector tube 250 can be broken into its implant portion 250i and its removable portion 250r, and the removable portion 250r and the insertion guide 280 can be removed. As a result, as shown in FIG. 15B, a channel 282 remains disposed through the device 210. This channel 282 can be occluded by any means known to those skilled in the art, or alternatively, if occlusion is not desired, the channel 282 can remain open to allow fluid to flow therethrough.

Figure 16A:
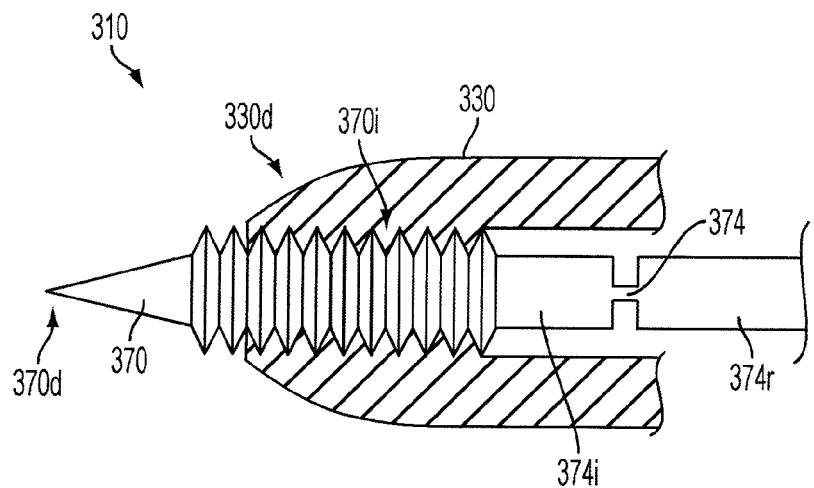
FIG. 16A is a side cross-sectional view of one exemplary embodiment of a distal end of an occlusion device prior to or during insertion into an opening or formation of a puncture in tissue.
Figure 16B:
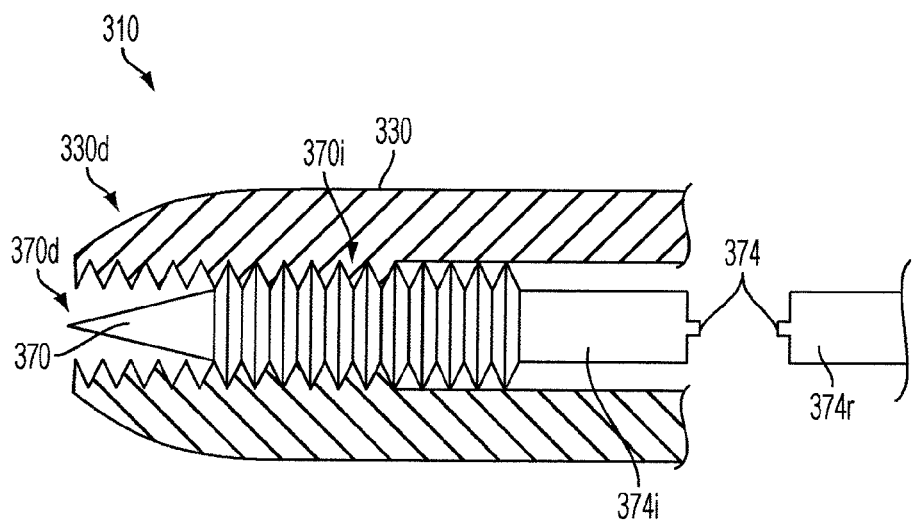
FIG. 16B is a side cross-sectional view of the distal end of the device of FIG. 16A after retraction of a distal tip of the distal end and separation of the distal end from a removable portion of the occlusion device.

FIGS. 16A and 16B illustrate a further occlusion device 310 having a distal tip 370 that is in the form of a pointed elongate shaft extending through the device 310 and out of a distal end 330d of the core pin 330. As shown, an intermediate portion 370i that is proximal to a terminal end 370d of the distal tip 370 is threaded and is configured to engage complementary threads disposed in a bore of the core pin 330. The distal tip 370 can be used to puncture tissue to create an opening in which to dispose the occlusion device 310. The distal tip 370 can be configured similar to the ejector tube 50 of the device 10 in that it can be frangible at a break point 374 so that an implant portion 374i can remain while a removable portion 374r can be removed. Following deployment of the device 310, as illustrated in FIG. 16B, the distal tip 370 can be rotated inside of the core pin 330 such that the distal tip 370 is fully disposed within the core pin 330. As shown, the distal tip 370 can still occlude the opening extending through the device 310.

Figure 17A:
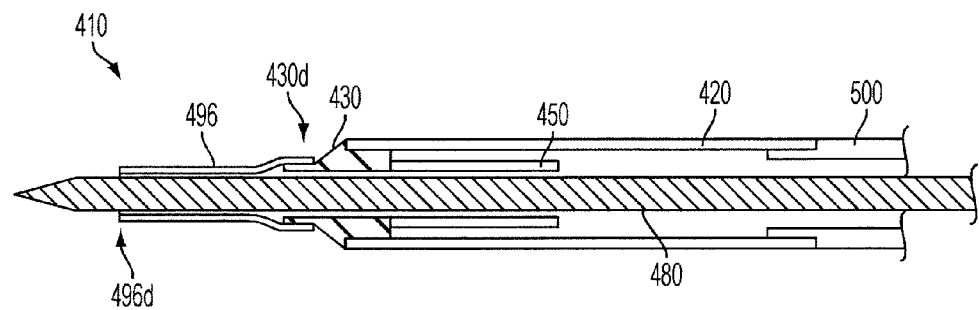
FIG. 17A is a side cross-sectional view of another exemplary embodiment of a deployment device in an initial, unformed configuration.
Figure 17B:
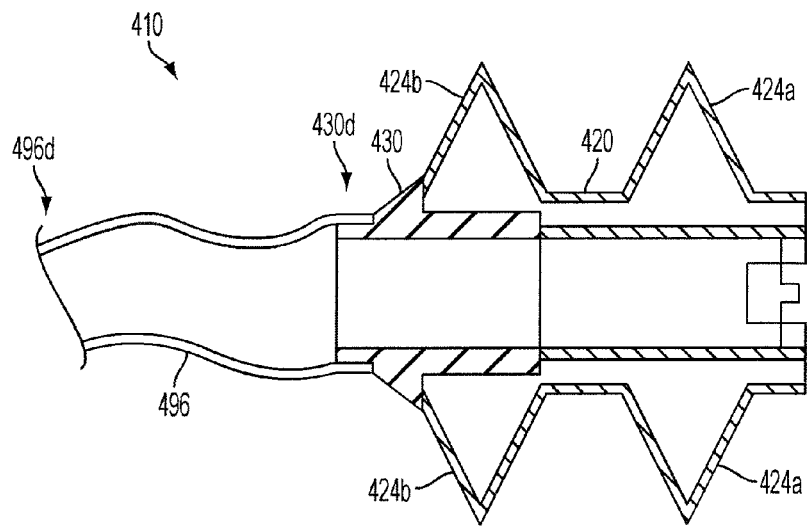
FIG. 17B is a side cross-sectional view of the device of FIG. 17A in a fully formed configuration.
Figure 18:
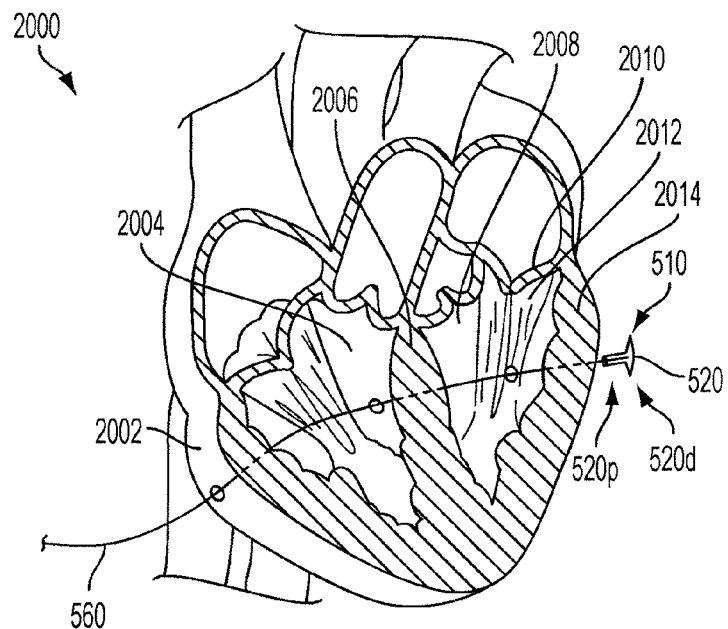
FIG. 18 is a schematic view of a heart having a leaking mitral valve to which a partially-deployed occlusion device is adjacent.

In another embodiment, the device can be modified to allow fluid flow therethrough. For example, an embodiment of a device having an implantable flexible tubular member extending from a distal end thereof is illustrated in FIGS. 17A and 17B. The implantable, flexible tubular member 496 is designed to be a fluid conduit, and thus this embodiment is generally not considered to be an occlusion device. As shown, and similar to the device 210, the insertion guide 480 extends through the device 410 and is connected to the ejector tube 450 disposed within the outer tubular body 420. The implantable flexible tubular body 496 is coupled to a distal end 430d of the core pin 430 and extends distally parallel to at least a portion of the insertion guide 480. After the tubular body 420 is deployed to form wings 424a and 424b, for instance by the insertion guide 480 and the former 500, the insertion guide 480 and former 500 can be removed so that the flexible tubular member 496 allows fluid to pass through the device 410. A distal end 496d of the tubular member 496 can be coupled to a fluid path as desired.

In an alternative embodiment, the flexible tubular member 496 can be coupled to the distal end 430d of the core pin 430 but can begin in an undeployed position in which it does not extend distally beyond the insertion guide 480. After the wings 424a, 424b of the outer tubular body 420 are deployed and the device 410 is secured in its desired location, the flexible tubular member 496 can be deployed to extend distally and function as described herein by sliding the insertion guide 480 in a proximal direction and separating it from the deployed device 410. In still a further alternative embodiment, the flexible tubular member 496 can be a deployable occlusion material that can be configured to deploy over the bore extending through the device 410 to occlude the bore. For example, after the insertion guide 480 is removed, the flexible tubular member 496 can be deployed to cover the bore of the device 410 and occlusion can result. Occlusion can also result simply by deploying the device 410 because the device 410 can significantly reduce the diameter of the opening in which it is disposed.

Although not illustrated, any of the alternative devices 110, 210, 310, and 410 can include a tether similar to tether 60 of device 10. The tether can be configured to be mated to any portion of the alternative devices, depending on whether it is desired to have the tether remain or be removed after the device has been deployed. Likewise, although not illustrated in devices 110, 210, 310, and 410 above, a slide tube similar to slide tube 40 of device 10 can be incorporated into these devices by a person skilled in the art. The slide tube can be attached to a proximal end of the tubular body 120, 220, 320, and 420 of each device 110, 210, 310, and 410.

Each of the components of the devices 10, 110, 210, 310, and 410 can be formed from a variety of materials. Thus, each of respective outer tubular bodies, core pins, slide tubes, ejector tubes, guide tips, insertion guides, locking mechanisms, and flexible tubular members can be formed from a variety of materials including absorbable and non-absorbable materials. Some of the materials can be the same for the different components, while other materials can be different. Exemplary materials include, by way of non-limiting example, any resorbable (e.g., biocompatible and/or bioabsorbable) materials, including, for example, titanium (and titanium alloys), magnesium alloys, stainless steel, polymeric materials (synthetic and/or natural), shape memory material such as Nitinol®, ceramic, etc. Materials which are not normally radiopaque, e.g., magnesium alloy, may be enhanced and made x-ray visible with the addition of x-ray visible materials, such as particles of iron oxide, stainless steel, titanium, tantalum, platinum, or any other suitable equivalents. Further, non-permeable materials, such as polyethylene terephthalate and polyvinylidene chloride, and semi-permeable materials, such as polylactide, can also be used to form the various components.

Generally the materials used for the core pins, slide tubes, ejector tubes, and locking mechanisms can be more rigid than the materials used for the outer tubular bodies, guide tips, insertion guides, and flexible tubular members. In one exemplary embodiment, an outer tubular body, a core pin, a slide tube, an ejector tube, and a guide tip are each formed from Stainless Steel grade 316VLM, an insertion guide is formed from a Stainless Steel wire, a locking mechanism is formed from Stainless Steel or Nitinol, and a flexible tubular member is formed from Stainless Steel. The tether can likewise be formed from a variety of materials, including both absorbable and non-absorbable materials. Exemplary materials include, by way of non-limiting example, polyglycolic acid, polylactic acid, polydioxanone, polypropylene, and nylon. In one exemplary embodiment, a tether is formed from Stainless Steel.

The size and shape of the components of the devices described herein can depend at least on the manner in which they will be used and the location in which they will be deployed. In the illustrated embodiments, the devices, and thus components thereof, are generally cylindrical in shape, although other shapes can be adapted for use without departing from the spirit of the invention. In one exemplary embodiment the device has a length L (FIG. 1) in the range of about 15 millimeters to about 25 millimeters and a diameter D (FIG. 1) in the range of about 1 millimeter to about 3 millimeters. In one embodiment, the length L of the device is about 18 millimeters and the diameter D is about 1.54 millimeters. Each of the components associated therewith can be sized and shaped accordingly.

The devices disclosed herein can be operated in a variety of manners, depending at least in part on the features incorporated therein. However, in one exemplary use of the occlusion device 10 of FIGS. 1-10, a former is coupled to the device 10 at the proximal end 20p of the outer tubular body 20 and the insertion guide 80 is disposed within a bore of a shaft of the former. The insertion guide 80 can be rotated and retracted proximally along the longitudinal axis of the device 10 to apply both a torsional force in a first direction $T_1$ and a compressive force in a proximal direction B to the occlusion device 10. The application of the torsional and compressive forces results in the core pin 30 moving proximally toward the slide tube 40 and the proximal wings 24a being deployed, as shown in FIG. 8. The wings 24a can be partially or fully deployed to achieve a desired configuration.

Once the proximal wings 24a are deployed, the insertion guide 80 can be rotated and retracted proximally along the longitudinal axis of the device 10 to apply both a torsional force in a second, opposite direction $T_2$ and a compressive force in the proximal direction B to the occlusion device 10. The application of the torsional and compressive forces results in the core pin 30 moving further distally toward the slide tube 40 and the distal wings 24b being deployed, as shown in FIG. 9. The wings 24b can be partially or fully deployed to achieve a desired configuration. In one exemplary embodiment, following deployment of the distal wings 24b, as shown in FIGS. 9 and 10, the distal end 50d of the ejector tube 50 abuts the proximal end 30p of the core pin 30.

After the occlusion device 10 is actuated to its desired configuration, the former, as well as a portion of the occlusion device, can be removed from the surgical site. This can be achieved by applying a tensile load to the system, thereby causing the ejector tube 50 to break at the break point 54. In the illustrated embodiment, the insertion guide 80 is retracted proximally to apply a tensile force in the proximal direction B to the ejector tube 50. While this load is being applied, a force in the opposite direction G is applied to the occlusion device 10 because the tubular body 20 and the slide tube 40 can no longer move in the proximal direction B as the proximal end of the occlusion device 10 abuts the distal end of the former, resulting in the force in the opposite direction G. As a result of these opposed forces in the directions B and G, the ejector tube 50 breaks at the break point 54 to separate the implant portion 50i and the removable portion 50r. As shown in FIG. 10, the insertion guide 80 and the removable portion 50r, along with the former (not shown), are removed while the distal tip 70, core pin 30, tubular body 20, slide tube 40, implant portion 50i, and tether 60 remain to occlude the opening in which the device 10 is disposed. Although not shown in FIGS. 1-10, the locking mechanism 90 can slidably couple to the tether 60. The locking mechanism 90 can be selectively locked on the tether to induce a tension therein to assist in maintaining a location of the occlusion device 10 as described herein and induce compression of tissue between the occlusion device 10 and the locking mechanism 90.

A number of different areas of the body can be treated using the devices and methods disclosed herein. For example, in an exemplary embodiment illustrated in FIGS. 18-21, any of the various occlusion devices disclosed herein can be used to repair a leaking mitral valve 2010 of a heart 2000. As shown, an occlusion device 510 akin to devices 10, 110, 210, 310, and 410 can be inserted through a wall 2002 of the heart 2000, across the right ventricle 2004, through the interventricular septum 2006, across the left ventricle 2008, through the papillary muscles 2012, and into the muscular wall 2014 of the left ventricle 2008 where the repair is desired. Prior to insertion of the device 510, a puncture-creating tool can be used to pre-form holes used to access the desired surgical site that are not naturally occurring in the body, or the device 510 can include a distal guide tip configured to form punctures in tissue, similar to the tip on devices 110, 210, 310, and 410.

The device 510 can be deployed as described above so that wings of an outer tubular body 520 engage tissue surrounding the device 510. For example, the outer elongate tubular body 520 of the device 510 can be positioned through an opening in the left ventricle 2008 to position distal slits on one side and proximal slits on the other. A rotational force in a first direction is applied to the tubular body 510 to expand the distal portion 520d of the body so that the distal wings engage the outer wall 2014 of the left ventricle 2008. Subsequently, a rotational force in a second, opposite direction is applied to the tubular body 510 to expand the proximal portion 520p of the body. Optionally, an axial force in the distal direction can be applied as either or both of the wings are rotated and expanded, thereby compressing a middle portion of the body 520 disposed therebetween. Any number of formers, insertion instruments, or deployment systems can be used to apply rotational and/or axial forces to the device 510.

Figure 19:
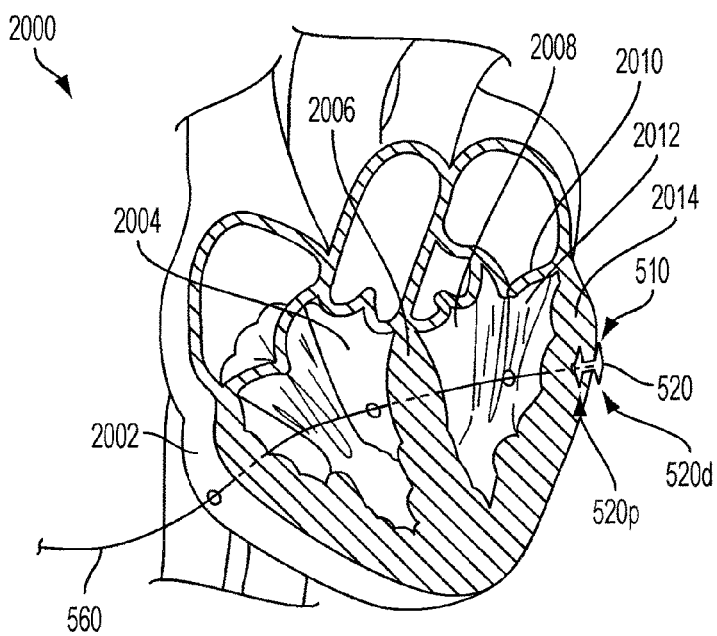
FIG. 19 is a schematic view of the heart of FIG. 18 in which the occlusion device is fully deployed and disposed within the heart.
Figure 20:
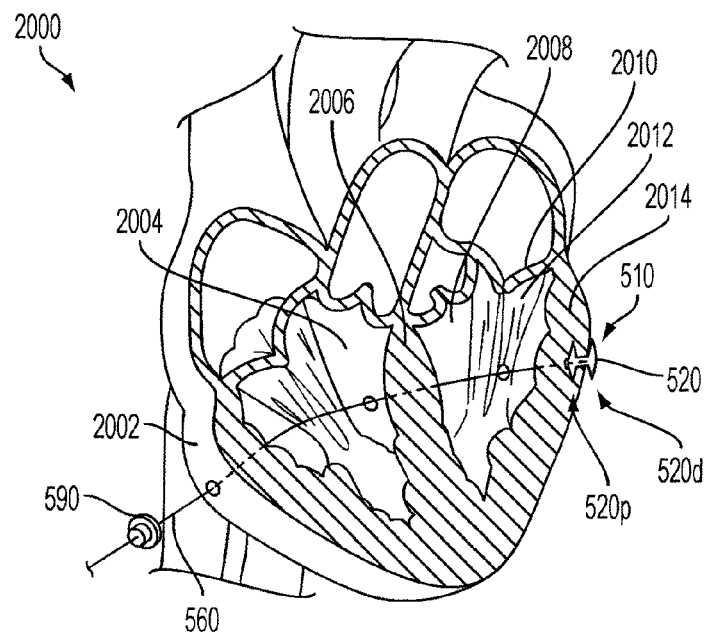
FIG. 20 is a schematic view of the heart of FIG. 19 in which a locking tool is coupled to a tether extending from the occlusion device, prior to locking the locking tool.
Figure 21:
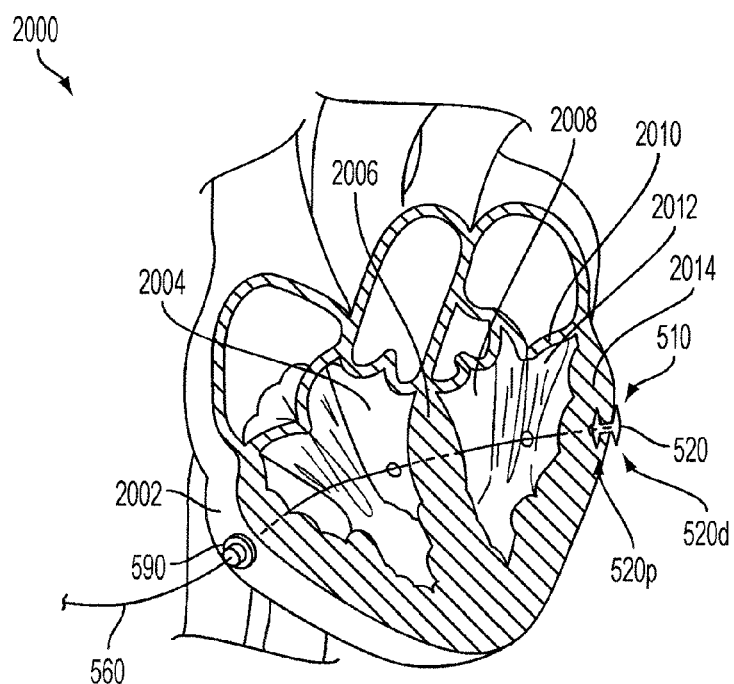
FIG. 21 is a schematic view of the heart of FIG. 20 in which the locking tool is locked.

Following deployment of the device 510 in the opening, as shown in FIG. 19, the instrument(s) used to deploy the device 510 can be removed from the surgical site. As shown, a tether 560 can be coupled to a portion of the device 510 that remains implanted in the opening. A locking mechanism 590 can be associated with a proximal end of the tether 560, as illustrated in FIG. 20. The locking mechanism 590 induces tension along the tether 560 by being selectively slid and locked along the tether 560. As tension in the tether 560 increases, the outer cardiac walls 2002 and 2014 are pulled closer together and thus the leaflets of the mitral valve 2010 are brought into coaptation, as shown in FIG. 21. A person skilled in the art will be able to determine the degree of coaptation desired to eliminate mitral valve regurgitation, and thus the amount of tension desired in the tether 560. The degree needed and the effect of the tension on the components of the heart can be judged, for example, using indirect imaging means such as transoesophageal echo cardiography, transthoracic echo cardiography, or other imaging means.

In some embodiments an insertion guide, similar to insertion guide 80, can be used to assist in deploying the device. Optionally, the insertion guide can remain attached to the device 510 even after implantation is complete. As a result, in an instance in which the elongate tubular body 520 is deployed within tissue in a sub-optimal position, the guide can be used to position the body 520 in a more desirable location. Such a guide can also be configured to be separable, similar to ejector tube 50, so a portion of the guide can be removed while another portion can remain coupled to the device 510. Further, in other embodiments, it can be preferable to predispose a guidewire through the path the device 510 is configured to go through. The device 510 can then be inserted using the guidewire to assist in locating the device 510 in the desired location. The tether 560 can likewise assist in implanting the device 510 at its desired location, even prior to disposing a locking mechanism onto it.

Figure 22:
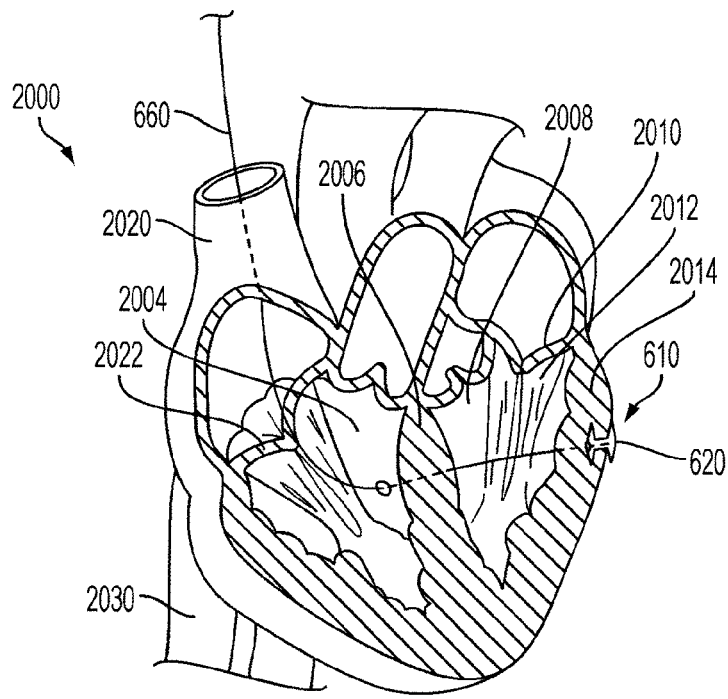
FIG. 22 is another schematic view of a heart having a leaking mitral valve in which an occlusion device is fully deployed.
Figure 23:
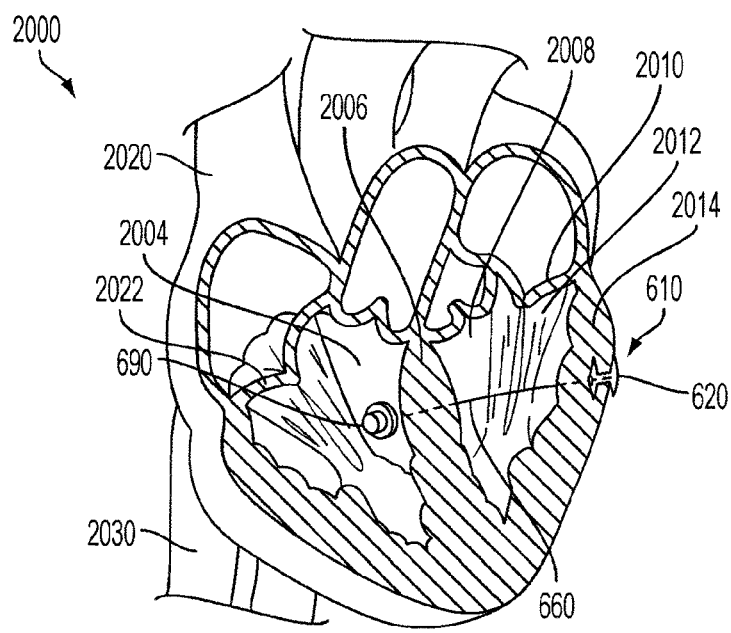
FIG. 23 is a schematic view of the heart of FIG. 22 in which a locking tool is coupled to a tether extending from the occlusion deice and is locked.

An alternative method for repairing a leaking mitral valve 2010 of a heart 2000 is shown in FIGS. 22 and 23. This method includes inserting a device 610 having an elongate tubular body 620 configured to expand as described herein through a vascular structure such as the superior or inferior vena cava 2020, 2030, advancing the device 610 through the tricuspid valve 2022, into the right ventricle 2004, across the interventricular septum 2006, across the left ventricle 2008, through the papillary muscles 2012, and into the muscular wall 2014 of left ventricle 2008. The device 610 can be deployed in a manner similar to the method of deployment described with respect to the device 510 such that the elongate tubular body 620 is deployed within or outside the left ventricle muscular wall 2014. The insertion instrument(s) used to deploy the device 610 can then be disconnected from the device, and a tether 660 attached to the portion of the device 610 remaining in the opening can extend from the elongate tubular body 620 in a proximal direction, across the ventricle chamber, and exit the heart 2000 out of the right ventricular side of the interventricular septum 2006.

A locking mechanism 690 can be coupled to the tether 660 and advanced along the tether 660 to tension the same. As the locking mechanism 690 is advanced distally to further tension the tether 660, the interventricular cardiac wall and the left ventricular wall are pulled closer together, and thus the mitral leaflets are brought into coaptation, as shown in FIG. 23. Any portion of the tether 660 that extends proximally from the locking mechanism 690 can be left in-situ and tunneled into a subcutaneous pouch formed, for instance, in the neck or subcalvicular region. By allowing the excess to remain, the tension in the tether 660 can be selectively re-adjusted at a later date by re-adjusting the locking mechanism 690. Alternatively, the excess tether 660 can be cut-away and removed from the body via the vascular structure.

Figure 24:
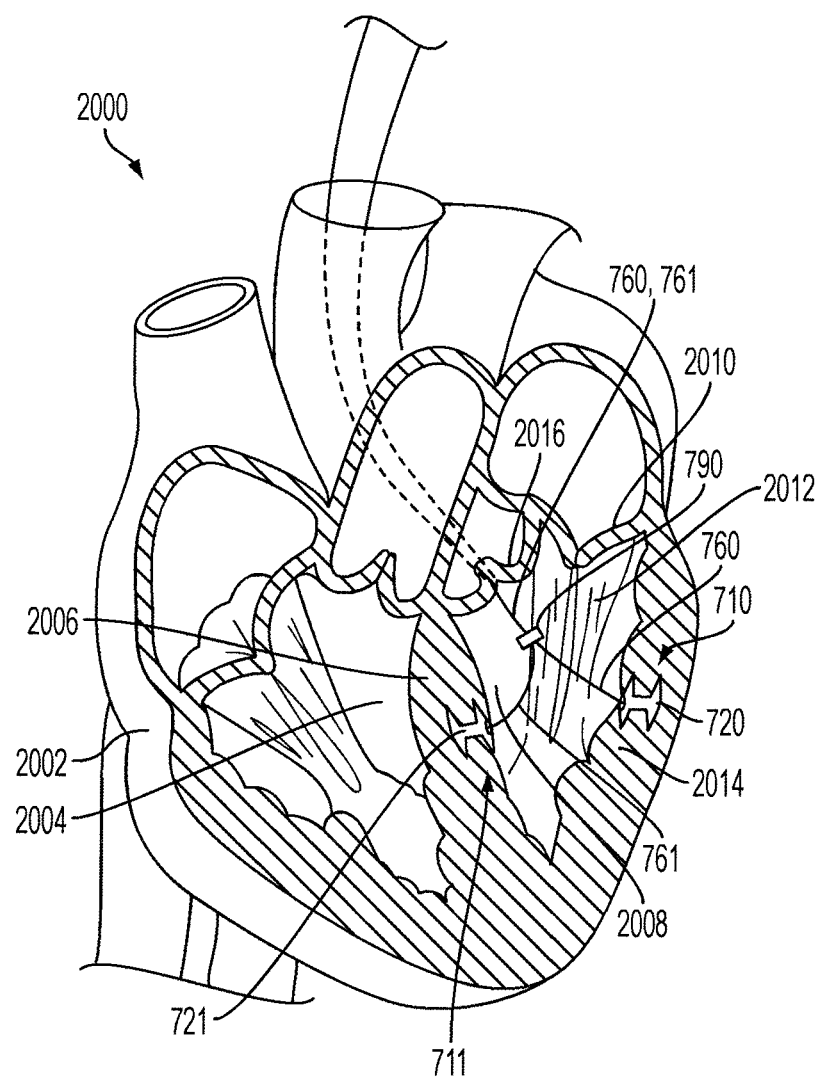
FIG. 24 is yet another schematic view of a heart having a leaking mitral valve in which multiple occlusion devices are deployed.

FIG. 24 illustrates yet a further method for repairing a leaking mitral valve 2010 in a heart 2000 using two or more occlusion devices. The method includes inserting a first device 710 having an elongate tubular body 720 configured to expand as described herein and a tether 760 attached thereto through an aortic valve 2016, into the left ventricle 2008, and then positioned either in the interventricular septum 2006 as shown or beyond the septum 2006 and anchored on the right ventricular side of the interventricular septum 2006, for example in the right ventricle 2004 or the outer cardiac wall 2002. Further, a second device 711 having an elongate tubular body 721 configured to expand as described herein and a tether 761 attached thereto is positioned either in the left ventricular muscle wall 2014 as shown or within the left ventricle 2008, such as in the papillary muscles 2012. Each of the tethers 760 and 761 can be connected by a locking mechanism 790 configured to slide along the tethers 760 and 761. As the locking mechanism 790 is slid distally along the tethers 760 and 761, the interventricular septum 2006 and the left ventricular wall 2014 are pulled closer together, and thus the leaflets of the mitral valve 2010 are brought into coaptation.

A person skilled in the art will understand that with any of the embodiments related to treating a mitral valve of a heart, other valves within the heart, or other valves within the body of a subject in general, can be treated in a similar manner. Likewise, although in the illustrated embodiments the devices are described as being inserted into a particular wall or chamber, a person skilled in the art will understand that the devices can be deployed in other portions of tissue in the region being treated so that the tissue can be pulled closer together to close the region being treated. Further, although particular paths are disclosed for guiding the devices into and through the heart, any number of paths can be used without departing from the spirit of the invention.

Figure 25:
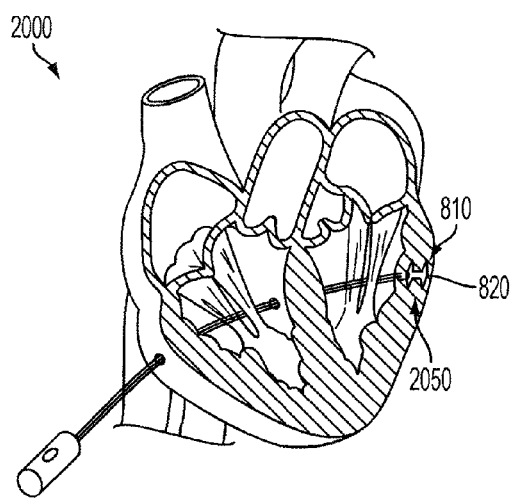
FIG. 25 is a schematic view of a heart having cardiac dysrhythmia in which an occlusion device is fully deployed.
Figure 26:
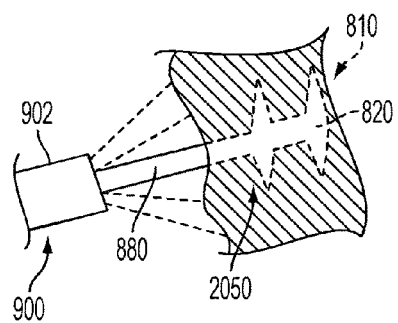
FIG. 26 is a schematic view of a former used in conjunction with delivery of the device of FIG. 25 illustrating use of the former to ablate tissue of the heart.
Figure 27:
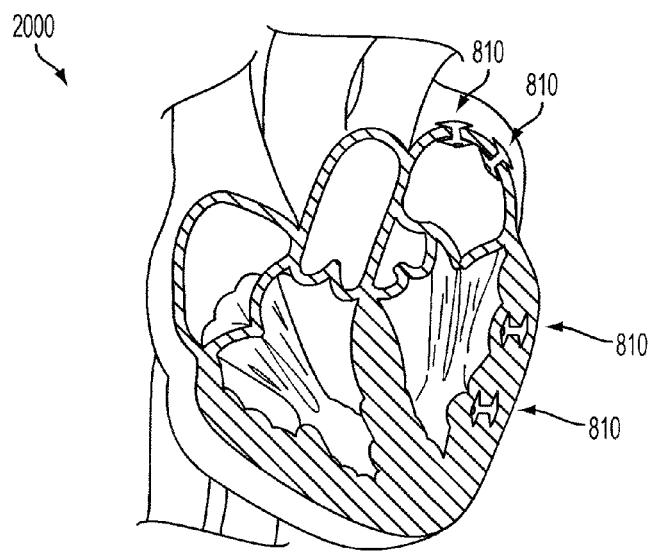
FIG. 27 is a schematic view of the heart of FIG. 25 in which multiple occlusion devices are deployed.

The devices and methods disclosed herein can also be used to treat irregular heartbeats, sometimes referred to as cardiac dysrhythmia. One example of a cardiac dysrhythmia is atrial fibrillation. As shown in FIGS. 25-27, after a site 2050 of the abnormal cardiac conduction pathway within the heart muscle 2000 is identified, a device 810 having an elongate tubular body 820 configured to expand as described herein can be inserted into the abnormal conduction site 2050 and deployed. Prior to detaching insertion instruments(s) from the device 810, one or more of the components of the instrument(s) can be used as an ablation catheter. For example, as illustrated in FIG. 26, an outer tube 902 of a former 900 can act as a single electrical pole. A second electrical pole can be formed by a back-plate (not shown) in contact with a subject's external body. By passing an electrical current such as a high voltage direct current or a radiofrequency source through the expanded elongated tubular body, the site 2050 of the abnormal electrical focus in the cardiac muscle is ablated. The insertion instrument(s) can then be detached from the device 810, leaving the device 810 implanted within the wall 2014 of the heart 2000 where the abnormal conduction site 2050 existed. As illustrated in FIG. 27, a plurality of devices 810 can be disposed in the heart muscle in this fashion to assist in treating cardiac dysrhythmia. Using the device 810 in this manner allows for a more complete transmural ablation of the cardiac tissue and also reduces the likelihood of perforation of the cardiac muscle due to the sealing nature of the deployed device 810.

Treatment is not limited to hearts. Other naturally existing openings, such as a fallopian tube, can be occluded using the devices and methods disclosed herein. Likewise, openings resulting from diseases or defects, or even openings created as part of a surgical procedure, can also be occluded in accordance with the devices and methods disclosed herein.

Figure 28:
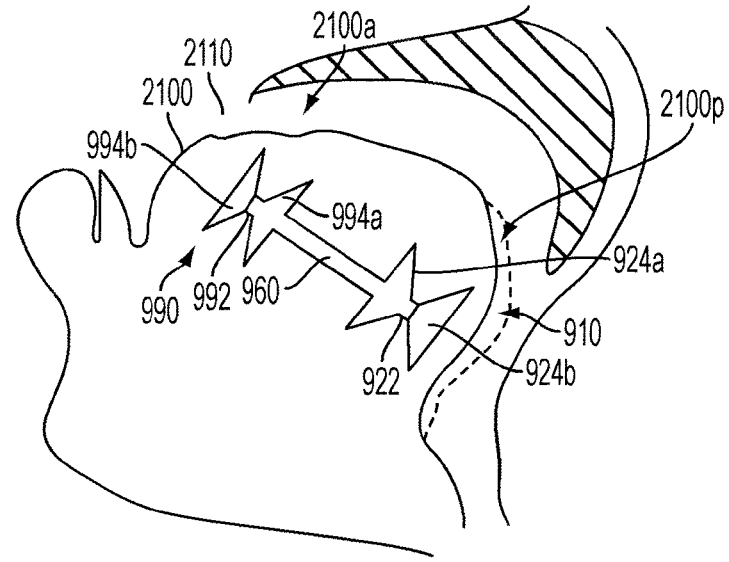
FIG. 28 is a schematic view of a region surrounding a tongue in which an occlusion device and a locking mechanism are disposed in the tongue.

By way of non-limiting example, a treatment for sleep apnea that includes delivering devices of the nature disclosed herein to a tongue 2100 is illustrated in FIG. 28. As shown, a device 910 having an elongate tubular body 920 configured to expand to form wings 924a and 924b as described herein and a tether 960 extending proximally therefrom is deployed in a posterior region 2100p of the tongue 2100. As shown, a locking mechanism 990 is coupled to the tether 960 and is located proximate to an anterior region 2100a of the tongue 2100. In the illustrated embodiment, the locking mechanism 990 also includes an elongate tubular body 992 having expandable wings 994a and 994b. In one embodiment the distal and proximal wings 924b and 924a of the elongate tubular body 920 are expanded, and then tension is applied to the tether 960 to cause a gap between the device 910 and the locking mechanism 990 to be reduced, preferably by drawing the device 910 toward the locking mechanism 990. This has the effect of opening the pharynx 2110, allowing more air to pass through the airway and into the lungs. Once a desired position is reached, proximal and distal wings 994a and 994b of the locking mechanism 990 can be expanded to secure the position of the device 910. Following deployment, any insertion instruments used to deploy either or both of the device 910 and the locking mechanism 990 can be detached and removed.

Figure 29:
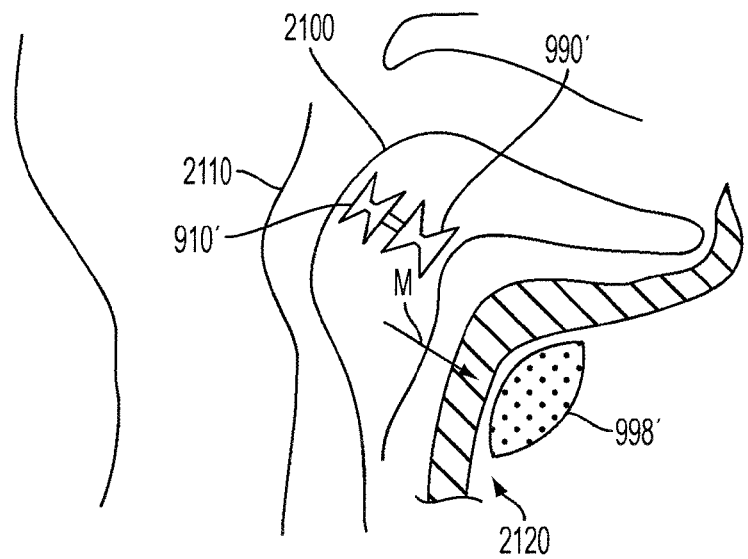
FIG. 29 is another schematic view of a region surrounding a tongue in which an occlusion device and a locking mechanism are disposed in the tongue and a magnetic source is disposed outside of a throat.

FIG. 29 illustrates a further method for treating sleep apnea using the devices and methods disclosed herein. The method for deploying the device 910' and the locking mechanism 990' in a tongue 2100 can be akin to the methods disclosed with respect to FIG. 28. In the embodiment illustrated in FIG. 29, however, one of either the device 910' or the locking mechanism 990' can include magnetic properties such that a magnetic source 998' provided in proximity to the device 910' or locking mechanism 990' can magnetically interact with the source 998'. As shown, the magnetic source 998' is disposed outside of a throat 2120 and is configured to pull the locking mechanism 990' toward it in a direction M. As a result, the tongue 2100 pulls away from the pharynx 2110 and the space in the airway for passage of air to the lungs increases.

Embodiments that are used to form a channel through an opening and thus do not occlude the opening, can also have a variety of applications. These embodiments include the devices 210 and 410, although a person skilled in the art will recognize that any of the occlusion devices and methods disclosed herein can be easily adapted to perform the opposite function of allowing fluid to flow through the device.

Figure 30:
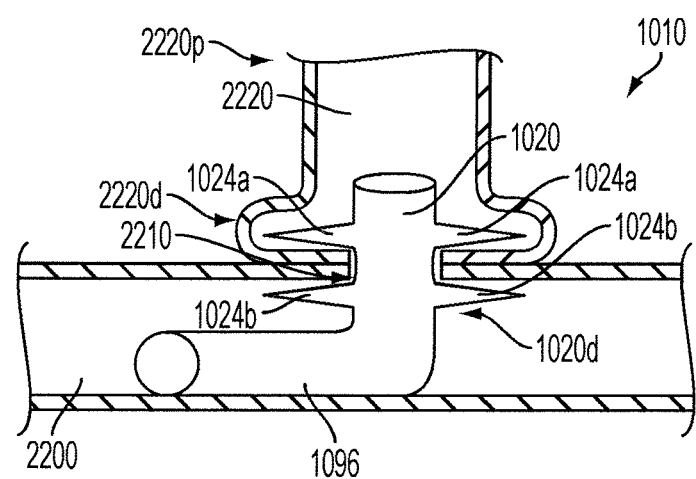
FIG. 30 is a schematic view of a coronary artery and a graft structure having a deployment device mated thereto to place the artery and graft structure in fluid communication.

One example of an embodiment in which a device is used to form a channel includes creating a junction between the end of a tubular body and a side wall of another tubular body. One such application is illustrated in FIG. 30, in which a device 1010 having an elongate tubular body 1020 configured to expand as described herein and a flexible tubular member 1096 extending from a distal end 1020d of the body 1020 creates a junction between a coronary artery 2200 and a graft structure 2220. The device 1010 can be inserted into the coronary artery 2200 such that the distal end 1020d of the body 1020 is located in the direction of fluid flow from the graft 2220. Distal wings 1024b of the body 1020 can first be deployed and then positioned adjacent to the puncture 2210. The graft 2220 can then be extended distally so a distal end 2220d thereof is in communication with the puncture 2210 in the coronary artery 2200. Subsequently, proximal wings 1024a of the body 1020 can be deployed, thereby locking and sealing the graft 2220 against the coronary artery 2200. Insertion instrument(s) used to deploy the device 1010 can then be detached from the device 1010 and withdrawn from the internal lumen of the graft 2220. The proximal end 2220p of the graft 2220 can then be attached to another source of blood flow. These procedures can be formed with a variety of blood vessels and graft structures.

One skilled in the art will appreciate further features and advantages of the invention based on the above-described embodiments. Accordingly, the invention is not to be limited by what has been particularly shown and described, except as indicated by the appended claims. For example, although components may be described as being separate but coupled to each other, a person skilled in the art will appreciate that some of these components can form a single component. Non-limiting examples include: the guide tip 70 and the core pin 30 of the device 10 and one or more of the removable portion 50r of the ejector tube 50, a former, and any delivery system associated therewith. Likewise, although components of a device may be described as being coupled to a particular component, components can be coupled to other portions in some instances. By way of non-limiting example, the guide tip 70 can be coupled to the core pin 30 as opposed to the implant portion 50i of the ejector tube 50. Sill further, a person skilled in the art will appreciate that the devices disclosed herein can be adapted for use in any of the techniques disclosed herein, and likewise, the techniques disclosed herein can be adapted for use in conjunction with any of the devices disclosed herein. All publications and references cited herein are expressly incorporated herein by reference in their entirety.

What is claimed is:

1. An occlusion device, comprising:

an outer elongate tubular body having proximal and distal portions, the proximal portion having a plurality of proximal slits formed therein and configured to allow the proximal portion to expand to form proximal wings, and the distal portion having a plurality of distal slits formed therein and configured to allow the distal portion to expand to form distal wings;

an elongate guide member extending distally from a distal end of the outer elongate tubular body and configured such that a proximal end of the guide member is disposed within the outer elongate tubular body and occludes fluid from passing through the expanded distal wings; and a slide tube disposed within the proximal portion of the outer elongate tubular body and having a proximal end fixedly mated to a proximal end of the outer elongate tubular body, the outer elongate tubular body being configured to move along an outer surface of the slide tube as the proximal and distal portions expand to form the proximal and distal wings, wherein a distal end of the slide tube abuts the proximal end of the guide member when the proximal and distal portions of the outer tubular body are expanded to form the proximal and distal wings.

2. The device of claim 1, further comprising a tether having a distal portion disposed within the outer elongate tubular body, and a proximal portion extending proximally from the proximal end of the outer elongate tubular body.

3. The device of claim 2, further comprising a locking tool coupled to the tether and configured to induce tension in the tether.

4. The device of claim 1, wherein the slide tube is configured to occlude fluid flow through the proximal wings when the proximal portion is expanded.

5. The device of claim 1, further comprising an inner elongate tubular body extending at least partially through the outer elongate tubular body and through the slide tube.

6. The device of claim 5, wherein a proximal end of the guide member is fixedly mated to a distal end of the inner elongate tubular body.

7. The device of claim 5, wherein the inner elongate tubular body has a distal end that is fixedly mated to a distal tip on a distal end of the outer elongate tubular body.

8. The device of claim 5, wherein the inner elongate tubular body includes a frangible portion formed thereon and configured to allow a proximal portion of the inner elongate tubular body to be separated from a distal portion of the elongate tubular body and from the outer elongate tubular body.

9. The device of claim 8, further comprising an insertion guide coupled to the proximal portion of the inner elongate tubular body, the insertion guide being configured to selectively expand and compress the outer elongate tubular body and activate the frangible portion of the inner elongate tubular body.

10. The device of claim 1, further comprising a distal tip disposed on a distal end of the guide member, the distal tip being closed to occlude fluid from flowing through the outer elongate tubular body.

11. The device of claim 1, wherein at least one of the guide member and the slide tube is closed to occlude fluid from flowing through the elongate tubular body.

12. The device of claim 1, wherein the slits in the proximal portion extend in a first direction around a circumference of the elongate tubular body, and the slits in the distal portion extend in a second, opposite direction around a circumference of the elongate tubular body.

13. The device of claim 1, wherein the proximal and distal portions are configured to expand in response to a torsional force applied thereto.

14. An occlusion device, comprising:
an outer elongate tubular body having proximal and distal portions, the proximal portion having a plurality of proximal slits formed therein and configured to allow the proximal portion to expand to form proximal wings, and the distal portion having a plurality of distal slits formed therein and configured to allow the distal portion to expand to form distal wings;
a guide member extending distally from a distal end of the outer elongate tubular body;
an inner elongate tubular body extending at least partially through the outer elongate tubular body; and
a slide tube disposed within the proximal portion of the outer elongate tubular body and configured to extend distally beyond the plurality of proximal slits to occlude fluid from passing through the expanded proximal wings, the slide tube having a proximal end fixedly mated to a proximal end of the outer elongate tubular body and a bore extending therethrough such that an inner surface of the slide tube exposed by the bore slides along an outer surface of the inner elongate tubular body, toward the guide member, as the proximal and distal portions expand to form the proximal and distal wings.

15. The occlusion device of claim 14, wherein a distal end of the slide tube abuts a proximal end of the guide member when the proximal and distal portions of the outer tubular body are expanded to form the proximal and distal wings.

16. The occlusion device of claim 14, further comprising a tether having a distal portion disposed within the outer elongate tubular body, and a proximal portion extending proximally from the proximal end of the outer elongate tubular body.

17. An occlusion device, comprising:
an outer elongate tubular body having proximal and distal portions, the proximal portion having a plurality of proximal slits formed therein and configured to allow the proximal portion to expand to form proximal wings, and the distal portion having a plurality of distal slits formed therein and configured to allow the distal portion to expand to form distal wings;
a guide member coupled to and extending distally from a distal end of the outer elongate tubular body, an elongate flexible distal member extending distally from the guide member and through a bore defined by the guide member, the guide member and flexible distal member being configured to occlude the distal end of the outer elongate tubular body;
a slide tube disposed within the proximal portion of the outer elongate tubular body and having a proximal end fixedly mated to a proximal end of the outer elongate tubular body, the outer elongate tubular body being configured to move along an outer surface of the slide tube as the proximal and distal portions expand to form the proximal and distal wings; and
a tether having a distal portion disposed within the outer elongate tubular body and extending through the slide tube, and having a proximal portion extending proximally beyond the proximal end of the outer elongate tubular body.

18. The occlusion device of claim 17, wherein a distal tip of the flexible distal member has a diameter that is larger than a diameter of an elongate tubular body of the flexible distal member.

* * * * *